(12) United States Patent  
Heller et al.

(10) Patent No.: US 8,142,642 B2  
(45) Date of Patent: *Mar. 27, 2012

(54) SMALL VOLUME IN VITRO ANALYTE SENSOR

(75) Inventors: Adam Heller, Austin, TX (US); Benjamin J. Feldman, Oakland, CA (US); James Say, Breckenridge, CO (US); Mark S. Vreeke, Granger, IN (US)

(73) Assignee: Abbott Diabetes Care Inc., Alameda, CA (US)

( * ) Notice: Subject to any disclaimer, the term of this patent is extended or adjusted under 35 U.S.C. 154(b) by 411 days.

This patent is subject to a terminal disclaimer.

(21) Appl. No.: 12/182,862

(22) Filed: Jul. 30, 2008

(65) Prior Publication Data

US 2009/0000960 A1 Jan. 1, 2009

Related U.S. Application Data

(60) Continuation of application No. 11/035,131, filed on Jan. 13, 2005, which is a division of application No. 10/457,585, filed on Jun. 9, 2003, now abandoned, which is a continuation of application No. 09/413,735, filed on Oct. 6, 1999, now Pat. No. 6,576,101, which is a division of application No. 08/795,767, filed on Feb. 6, 1997, now abandoned.

(51) Int. Cl.  
*G01N 27/327* (2006.01)

(52) U.S. Cl. .................. 205/792; 205/777.5

(58) Field of Classification Search .......... 204/403.01–403.15; 205/777.5, 205/778, 792  
See application file for complete search history.

(56) References Cited

U.S. PATENT DOCUMENTS 3,260,656 A 7/1966 Ross, Jr.  
(Continued)

FOREIGN PATENT DOCUMENTS

DE 4234553 4/1993  
(Continued)

OTHER PUBLICATIONS

JPO computer translation of Osamu et al. (JP 06-130032).

(Continued)

*Primary Examiner* — Alex Noguerola  
(74) *Attorney, Agent, or Firm* — Edward J. Baba; Shweta Chandra; Bozicevic, Field & Francis LLP

(57) ABSTRACT

A sensor designed to determine the amount and concentration of analyte in a sample having a volume of less than about 1 μL. The sensor has a working electrode coated with a non-leachable redox mediator. The redox mediator acts as an electron transfer agent between the analyte and the electrode. In addition, a second electron transfer agent, such as art enzyme, can be added to facilitate the electrooxidation or etectroreduction of the analyte. The redox mediator is typically a redox compound bound to a polymer. The preferred redox mediators are air-oxidizable. The amount of analyte can be determined by coulometry. One particular coulometric technique includes the measurement of the current between the working electrode and a counter or reference electrode at two or more times. The charge passed by this current to or from the analyte is correlated with the amount of analyte in the sample. Other electrochemical detection methods, such as arnperometric, voltammetric and potentiometric techniques, can also be used. The invention can be used to determine the concentration of a biomolecute, such as glucose or lactate, in a biological fluid, such as blood or serum. An enzyme capable of catalyzing the electrooxidation or electroreduction of the biomolecute is provided as a second electron transfer agent.

57 Claims, 10 Drawing Sheets

U.S. PATENT DOCUMENTS

| | | | |
|---|---|---|---|
| 3,506,544 A | 4/1970 | Silverman et al. | |
| 3,623,960 A | 11/1971 | Williams | |
| 3,653,841 A | 4/1972 | Klein | |
| 3,719,564 A | 3/1973 | Lilly, Jr. et al. | |
| 3,776,832 A | 12/1973 | Oswin et al. | |
| 3,837,339 A | 9/1974 | Aisenberg et al. | |
| 3,926,760 A | 12/1975 | Allen et al. | |
| 3,972,320 A | 8/1976 | Kalman | |
| 3,979,274 A | 9/1976 | Newman | |
| 4,008,717 A | 2/1977 | Kowarski | |
| 4,016,866 A | 4/1977 | Lawton | |
| 4,055,175 A | 10/1977 | Clemens et al. | |
| 4,059,406 A | 11/1977 | Fleet | |
| 4,076,596 A | 2/1978 | Connery et al. | |
| 4,098,574 A | 7/1978 | Dappen | |
| 4,100,048 A | 7/1978 | Pompei et al. | |
| 4,120,205 A | 10/1978 | Ripphahn et al. | |
| 4,133,735 A | 1/1979 | Afromowitz et al. | |
| 4,151,845 A | 5/1979 | Clemens | |
| 4,168,205 A | 9/1979 | Danninger et al. | |
| 4,172,770 A | 10/1979 | Semersky et al. | |
| 4,178,916 A | 12/1979 | McNamara | |
| 4,206,755 A | 6/1980 | Klein | |
| 4,210,156 A | 7/1980 | Bennett | |
| 4,216,245 A | 8/1980 | Johnson | |
| 4,224,125 A | 9/1980 | Nakamura et al. | |
| 4,225,410 A * | 9/1980 | Pace | 204/412 |
| 4,240,438 A | 12/1980 | Updike et al. | |
| 4,240,889 A | 12/1980 | Yoda et al. | |
| 4,244,800 A | 1/1981 | Frazzini et al. | |
| 4,247,297 A | 1/1981 | Berti et al. | |
| 4,271,119 A | 6/1981 | Columbus | |
| 4,318,784 A | 3/1982 | Higgins et al. | |
| 4,339,317 A | 7/1982 | Meiattini et al. | |
| 4,340,458 A | 7/1982 | Lemer et al. | |
| 4,352,960 A | 10/1982 | Dormer et al. | |
| 4,356,074 A | 10/1982 | Johnson | |
| 4,365,637 A | 12/1982 | Johnson | |
| 4,366,033 A | 12/1982 | Richter et al. | |
| 4,375,399 A | 3/1983 | Havas et al. | |
| 4,384,586 A | 5/1983 | Christiansen | |
| 4,388,166 A | 6/1983 | Suzuki et al. | |
| 4,390,621 A | 6/1983 | Bauer | |
| 4,392,933 A | 7/1983 | Nakamura et al. | |
| 4,401,122 A | 8/1983 | Clark, Jr. | |
| 4,404,066 A | 9/1983 | Johnson | |
| 4,407,959 A | 10/1983 | Tsuji et al. | |
| 4,418,148 A | 11/1983 | Oberhardt | |
| 4,420,564 A | 12/1983 | Tsuji et al. | |
| 4,427,770 A | 1/1984 | Chen et al. | |
| 4,431,004 A | 2/1984 | Bessman et al. | |
| 4,436,094 A | 3/1984 | Cerami | |
| 4,440,175 A | 4/1984 | Wilkins | |
| 4,444,892 A | 4/1984 | Malmros | |
| 4,450,842 A | 5/1984 | Zick et al. | |
| 4,458,686 A | 7/1984 | Clark, Jr. | |
| 4,461,691 A | 7/1984 | Frank | |
| 4,462,405 A | 7/1984 | Ehrlich | |
| 4,469,110 A | 9/1984 | Slama | |
| 4,477,314 A | 10/1984 | Richter et al. | |
| 4,483,924 A | 11/1984 | Tsuji et al. | |
| 4,484,987 A | 11/1984 | Gough | |
| 4,490,464 A | 12/1984 | Gorton et al. | |
| 4,492,622 A | 1/1985 | Kuypers | |
| 4,496,454 A | 1/1985 | Berger | |
| 4,522,690 A | 6/1985 | Venkatasetty | |
| 4,524,114 A | 6/1985 | Samuels et al. | |
| 4,526,661 A | 7/1985 | Steckhan et al. | |
| 4,534,356 A | 8/1985 | Papadakis | |
| 4,538,616 A | 9/1985 | Rogoff | |
| 4,543,955 A | 10/1985 | Schroeppel | |
| 4,545,382 A | 10/1985 | Higgins et al. | |
| 4,552,840 A | 11/1985 | Riffer | |
| 4,560,534 A | 12/1985 | Kung et al. | |
| 4,571,292 A | 2/1986 | Liu et al. | |
| 4,573,994 A | 3/1986 | Fischell et al. | |
| 4,581,336 A | 4/1986 | Malloy et al. | |
| 4,595,011 A | 6/1986 | Phillips | |
| 4,595,479 A | 6/1986 | Kimura et al. | |
| 4,619,754 A | 10/1986 | Niki et al. | |
| 4,627,445 A | 12/1986 | Garcia et al. | |
| 4,627,908 A | 12/1986 | Miller | |
| 4,629,563 A | 12/1986 | Wrasidlo | |
| 4,633,878 A | 1/1987 | Bombardieri | |
| 4,637,403 A | 1/1987 | Garcia et al. | |
| 4,650,547 A | 3/1987 | Gough | |
| 4,653,513 A | 3/1987 | Dombrowski | |
| 4,654,197 A | 3/1987 | Lilja et al. | |
| 4,655,880 A | 4/1987 | Liu | |
| 4,655,885 A | 4/1987 | Hill et al. | |
| 4,671,288 A | 6/1987 | Gough | |
| 4,679,562 A | 7/1987 | Luksha | |
| 4,680,268 A | 7/1987 | Clark, Jr. | |
| 4,682,602 A | 7/1987 | Prohaska | |
| 4,684,537 A | 8/1987 | Graetzel et al. | |
| 4,685,463 A | 8/1987 | Williams | |
| 4,703,756 A | 11/1987 | Gough et al. | |
| 4,711,245 A | 12/1987 | Higgins et al. | |
| 4,717,673 A | 1/1988 | Wrighton et al. | |
| 4,721,601 A | 1/1988 | Wrighton et al. | |
| 4,721,677 A | 1/1988 | Clark, Jr. | |
| 4,726,378 A | 2/1988 | Kaplan | |
| 4,726,716 A | 2/1988 | McGuire | |
| 4,750,496 A | 6/1988 | Reinhart et al. | |
| 4,757,022 A | 7/1988 | Shults et al. | |
| 4,758,323 A | 7/1988 | Davis et al. | |
| 4,759,371 A | 7/1988 | Franetzki | |
| 4,759,828 A | 7/1988 | Young et al. | |
| 4,764,416 A | 8/1988 | Ueyama et al. | |
| 4,764,485 A | 8/1988 | Loughran et al. | |
| 4,776,944 A | 10/1988 | Janata et al. | |
| 4,781,798 A | 11/1988 | Gough | |
| 4,784,736 A | 11/1988 | Lonsdale et al. | |
| 4,787,398 A | 11/1988 | Garcia et al. | |
| 4,795,707 A | 1/1989 | Niiyama et al. | |
| 4,796,634 A | 1/1989 | Huntsman et al. | |
| 4,805,624 A | 2/1989 | Yao et al. | |
| 4,813,424 A | 3/1989 | Wilkins et al. | |
| 4,815,469 A | 3/1989 | Cohen et al. | |
| 4,820,399 A | 4/1989 | Senda et al. | |
| 4,822,337 A | 4/1989 | Newhouse et al. | |
| RE32,922 E | 5/1989 | Levin et al. | |
| 4,830,959 A | 5/1989 | McNeil et al. | |
| 4,832,797 A | 5/1989 | Vadgama et al. | |
| RE32,947 E | 6/1989 | Dormer et al. | |
| 4,840,893 A | 6/1989 | Hill et al. | |
| 4,848,351 A | 7/1989 | Finch | |
| 4,871,351 A | 10/1989 | Feingold | |
| 4,871,440 A | 10/1989 | Nagata et al. | |
| 4,874,500 A | 10/1989 | Madou et al. | |
| 4,890,620 A | 1/1990 | Gough | |
| 4,894,137 A | 1/1990 | Takizawa et al. | |
| 4,895,147 A | 1/1990 | Bodicky et al. | |
| 4,895,479 A | 1/1990 | Michaelsen et al. | |
| 4,897,162 A | 1/1990 | Lewandowski et al. | |
| 4,897,173 A | 1/1990 | Nankai et al. | |
| 4,909,908 A | 3/1990 | Ross et al. | |
| 4,911,794 A | 3/1990 | Parce et al. | |
| 4,917,274 A | 4/1990 | Asa et al. | |
| 4,917,800 A | 4/1990 | Lonsdale et al. | |
| 4,919,141 A | 4/1990 | Zier et al. | |
| 4,919,767 A | 4/1990 | Vadgama et al. | |
| 4,923,586 A | 5/1990 | Katayama et al. | |
| 4,927,516 A | 5/1990 | Yamaguchi et al. | |
| 4,934,369 A | 6/1990 | Maxwell | |
| 4,935,105 A | 6/1990 | Churchouse | |
| 4,935,345 A | 6/1990 | Guilbeau et al. | |
| 4,936,956 A | 6/1990 | Wrighton | |
| 4,938,860 A | 7/1990 | Wogoman | |
| 4,942,127 A | 7/1990 | Wada et al. | |
| 4,944,299 A | 7/1990 | Silvian et al. | |
| 4,945,045 A | 7/1990 | Forrest et al. | |
| 4,950,378 A | 8/1990 | Nagata et al. | |
| 4,953,552 A | 9/1990 | DeMarzo | |
| 4,954,129 A | 9/1990 | Giuliani et al. | |
| 4,968,400 A | 11/1990 | Shimomura et al. | |
| 4,969,468 A | 11/1990 | Byers et al. | |

| | | | | | | |
|---|---|---|---|---|---|---|
| 4,970,145 A | 11/1990 | Bennetto et al. | | 5,310,885 A | 5/1994 | Maier et al. |
| 4,974,929 A | 12/1990 | Curry | | 5,312,527 A | 5/1994 | Mikkelsen et al. |
| 4,986,271 A | 1/1991 | Wilkins et al. | | 5,318,584 A | 6/1994 | Lange et al. |
| 4,994,167 A | 2/1991 | Shults et al. | | 5,320,098 A | 6/1994 | Davidson |
| 5,001,054 A | 3/1991 | Wagner | | 5,320,725 A | 6/1994 | Gregg et al. |
| 5,025,798 A | 6/1991 | Schindele | | 5,320,732 A | 6/1994 | Nankai et al. |
| 5,034,192 A | 7/1991 | Wrighton et al. | | 5,322,063 A | 6/1994 | Allen et al. |
| 5,037,527 A | 8/1991 | Hayashi et al. | | 5,325,853 A | 7/1994 | Morris et al. |
| 5,058,592 A | 10/1991 | Whistler | | 5,326,449 A | 7/1994 | Cunningham |
| 5,059,290 A | 10/1991 | Uchiyama et al. | | 5,337,747 A | 8/1994 | Neftel |
| 5,070,535 A | 12/1991 | Hochmair et al. | | 5,352,348 A | 10/1994 | Young et al. |
| 5,078,854 A | 1/1992 | Burgess et al. | | 5,352,351 A | 10/1994 | White et al. |
| 5,082,550 A | 1/1992 | Rishpan et al. | | 5,354,447 A | 10/1994 | Uenoyama et al. |
| 5,082,786 A | 1/1992 | Nakamoto | | 5,356,786 A | 10/1994 | Heller et al. |
| 5,089,112 A | 2/1992 | Skotheim et al. | | 5,364,797 A | 11/1994 | Olson et al. |
| 5,089,320 A | 2/1992 | Straus et al. | | 5,366,609 A | 11/1994 | White et al. |
| 5,094,951 A | 3/1992 | Rosenberg | | 5,368,028 A | 11/1994 | Palti |
| 5,095,407 A | 3/1992 | Kanezawa et al. | | 5,372,133 A | 12/1994 | Hogen Esch |
| 5,095,904 A | 3/1992 | Seligman et al. | | 5,376,251 A | 12/1994 | Kaneko et al. |
| 5,096,560 A | 3/1992 | Takai et al. | | 5,378,628 A | 1/1995 | Gratzel et al. |
| 5,096,836 A | 3/1992 | Macho et al. | | 5,380,422 A | 1/1995 | Negishi et al. |
| 5,101,814 A | 4/1992 | Palti | | 5,382,346 A | 1/1995 | Uenoyama et al. |
| 5,104,813 A | 4/1992 | Besemer et al. | | 5,387,327 A | 2/1995 | Khan |
| 5,108,564 A | 4/1992 | Szuminsky et al. | | 5,387,329 A | 2/1995 | Foos et al. |
| 5,108,889 A | 4/1992 | Smith et al. | | 5,390,671 A | 2/1995 | Lord et al. |
| 5,109,850 A | 5/1992 | Blanco et al. | | 5,391,250 A | 2/1995 | Cheney, II et al. |
| 5,112,455 A | 5/1992 | Cozzette et al. | | 5,393,903 A | 2/1995 | Gratzel et al. |
| 5,120,420 A | 6/1992 | Nankai et al. | | 5,395,504 A | 3/1995 | Saurer et al. |
| 5,120,421 A | 6/1992 | Glass et al. | | 5,411,647 A | 5/1995 | Johnson et al. |
| 5,126,034 A | 6/1992 | Carter et al. | | 5,413,690 A | 5/1995 | Kost et al. |
| 5,126,247 A | 6/1992 | Palmer et al. | | 5,422,246 A | 6/1995 | Koopal et al. |
| 5,128,015 A | 7/1992 | Szuminsky et al. | | 5,424,035 A | 6/1995 | Hones et al. |
| 5,130,009 A | 7/1992 | Marsoner et al. | | 5,437,973 A | 8/1995 | Vadgama et al. |
| 5,133,856 A | 7/1992 | Yamaguchi et al. | | 5,437,999 A | 8/1995 | Diebold et al. |
| 5,135,003 A | 8/1992 | Souma et al. | | 5,438,271 A | 8/1995 | White et al. |
| 5,140,393 A | 8/1992 | Hijikihigawa et al. | | 5,469,846 A | 11/1995 | Khan |
| 5,141,868 A | 8/1992 | Shanks et al. | | 5,478,751 A | 12/1995 | Oosta et al. |
| 5,161,532 A | 11/1992 | Joseph | | 5,494,562 A | 2/1996 | Maley et al. |
| 5,165,407 A | 11/1992 | Wilson et al. | | 5,496,453 A | 3/1996 | Uenoyama et al. |
| 5,168,046 A | 12/1992 | Hamamoto et al. | | 5,497,772 A | 3/1996 | Schulman et al. |
| 5,174,291 A | 12/1992 | Schoonen et al. | | 5,501,956 A | 3/1996 | Wada et al. |
| 5,185,256 A | 2/1993 | Nankai et al. | | 5,502,396 A | 3/1996 | Desarzens et al. |
| 5,190,041 A | 3/1993 | Palti | | 5,507,288 A | 4/1996 | Bocker et al. |
| 5,192,415 A | 3/1993 | Yoshioka et al. | | 5,508,171 A | 4/1996 | Walling et al. |
| 5,192,416 A | 3/1993 | Wang et al. | | 5,508,200 A | 4/1996 | Tiffany et al. |
| 5,198,367 A | 3/1993 | Aizawa et al. | | 5,509,410 A | 4/1996 | Hill et al. |
| 5,200,051 A | 4/1993 | Cozzette et al. | | 5,510,266 A | 4/1996 | Bonner et al. |
| 5,201,324 A | 4/1993 | Swierczek | | 5,512,159 A | 4/1996 | Yoshioka et al. |
| 5,202,261 A | 4/1993 | Musho et al. | | 5,514,253 A | 5/1996 | Davis et al. |
| 5,205,920 A | 4/1993 | Oyama et al. | | 5,518,006 A | 5/1996 | Mawhirt et al. |
| 5,206,145 A | 4/1993 | Cattell | | 5,520,787 A | 5/1996 | Hanagan et al. |
| 5,206,147 A | 4/1993 | Hoenes | | 5,525,511 A | 6/1996 | D'Costa |
| 5,208,154 A | 5/1993 | Weaver et al. | | 5,526,120 A | 6/1996 | Jina et al. |
| 5,209,229 A | 5/1993 | Gilli | | 5,531,878 A | 7/1996 | Vadgama et al. |
| 5,217,480 A | 6/1993 | Haber et al. | | 5,545,191 A | 8/1996 | Mann et al. |
| 5,217,595 A | 6/1993 | Smith et al. | | 5,547,555 A | 8/1996 | Schwartz et al. |
| 5,223,321 A * | 6/1993 | Sinnadurai et al. ............ 428/138 | | 5,552,027 A | 9/1996 | Birkle et al. |
| 5,227,042 A | 7/1993 | Zawodzinski et al. | | 5,556,524 A | 9/1996 | Albers |
| 5,229,282 A | 7/1993 | Yoshioka et al. | | 5,560,357 A | 10/1996 | Faupel et al. |
| 5,230,786 A | 7/1993 | Preidel | | 5,565,085 A | 10/1996 | Ikeda et al. |
| 5,250,439 A * | 10/1993 | Musho et al. ............ 205/778 | | 5,567,302 A | 10/1996 | Song et al. |
| 5,262,035 A * | 11/1993 | Gregg et al. ............ 204/403.11 | | 5,568,806 A | 10/1996 | Cheney, II et al. |
| 5,262,305 A | 11/1993 | Heller et al. | | 5,569,186 A | 10/1996 | Lord et al. |
| 5,264,103 A | 11/1993 | Yoshioka et al. | | 5,575,403 A | 11/1996 | Charlton et al. |
| 5,264,104 A | 11/1993 | Gregg et al. | | 5,575,895 A | 11/1996 | Ikeda et al. |
| 5,264,105 A | 11/1993 | Gregg et al. | | 5,580,527 A | 12/1996 | Bell et al. |
| 5,264,106 A | 11/1993 | McAleer et al. | | 5,582,184 A | 12/1996 | Erickson et al. |
| 5,266,179 A | 11/1993 | Nankai et al. | | 5,582,697 A | 12/1996 | Ikeda et al. |
| 5,271,815 A | 12/1993 | Wong | | 5,582,698 A | 12/1996 | Flaherty et al. |
| 5,272,060 A | 12/1993 | Hamamoto et al. | | 5,586,553 A | 12/1996 | Halili et al. |
| 5,276,294 A | 1/1994 | Jalbert | | 5,589,045 A | 12/1996 | Hyodo |
| 5,278,079 A | 1/1994 | Gubinski et al. | | 5,589,326 A | 12/1996 | Deng et al. |
| 5,279,294 A | 1/1994 | Anderson et al. | | 5,593,852 A | 1/1997 | Heller et al. |
| 5,280,551 A * | 1/1994 | Bowen ............ 385/53 | | 5,595,479 A | 1/1997 | Hansen et al. |
| 5,286,362 A | 2/1994 | Hoenes et al. | | 5,596,150 A | 1/1997 | Amdt et al. |
| 5,286,364 A | 2/1994 | Yacynych et al. | | 5,601,694 A | 2/1997 | Maley et al. |
| 5,288,636 A | 2/1994 | Pollmann et al. | | 5,611,900 A | 3/1997 | Worden et al. |
| 5,293,546 A | 3/1994 | Tadros et al. | | 5,617,851 A | 4/1997 | Lipkovker |
| 5,298,144 A | 3/1994 | Spokane | | 5,628,890 A | 5/1997 | Carter et al. |

| | | |
|---|---|---|
| 5,630,986 A | 5/1997 | Charlton et al. |
| 5,632,410 A | 5/1997 | Moulton et al. |
| 5,650,002 A | 7/1997 | Bolt |
| 5,650,062 A | 7/1997 | Ikeda et al. |
| 5,651,869 A | 7/1997 | Yoshioka et al. |
| 5,653,863 A | 8/1997 | Genshaw et al. |
| 5,658,443 A | 8/1997 | Yamamoto et al. |
| 5,660,163 A | 8/1997 | Schulman et al. |
| 5,666,966 A | 9/1997 | Horie et al. |
| 5,670,031 A | 9/1997 | Hintsche et al. |
| 5,680,858 A | 10/1997 | Hansen et al. |
| 5,682,233 A | 10/1997 | Brinda |
| 5,682,884 A | 11/1997 | Hill et al. |
| 5,686,829 A | 11/1997 | Girault |
| 5,695,623 A | 12/1997 | Michel et al. |
| 5,695,947 A | 12/1997 | Guo et al. |
| 5,700,695 A | 12/1997 | Yassinzadeh et al. |
| 5,707,502 A | 1/1998 | McCaffrey et al. |
| 5,708,247 A | 1/1998 | McAleer et al. |
| 5,711,861 A | 1/1998 | Ward et al. |
| 5,711,862 A | 1/1998 | Sakoda et al. |
| 5,720,862 A | 2/1998 | Hamamoto et al. |
| 5,723,345 A | 3/1998 | Yamauchi et al. |
| 5,726,565 A * | 3/1998 | Uchiyama et al. ............... 324/94 |
| 5,727,548 A | 3/1998 | Hill et al. |
| 5,736,029 A | 4/1998 | Pinkowski |
| 5,741,211 A | 4/1998 | Renirie et al. |
| 5,741,688 A | 4/1998 | Oxenboll et al. |
| 5,743,861 A | 4/1998 | Columbus et al. |
| 5,746,217 A | 5/1998 | Erickson et al. |
| 5,767,480 A | 6/1998 | Anglin et al. |
| 5,770,028 A | 6/1998 | Maley et al. |
| 5,781,455 A | 7/1998 | Hyodo |
| 5,786,584 A | 7/1998 | Button et al. |
| 5,791,344 A | 8/1998 | Schulman et al. |
| 5,798,031 A | 8/1998 | Charlton et al. |
| 5,800,420 A | 9/1998 | Gross et al. |
| 5,801,057 A * | 9/1998 | Smart et al. ..................... 436/68 |
| 5,804,048 A | 9/1998 | Wong et al. |
| 5,807,375 A | 9/1998 | Gross et al. |
| 5,820,551 A | 10/1998 | Hill et al. |
| 5,820,570 A | 10/1998 | Erickson et al. |
| 5,820,622 A | 10/1998 | Gross et al. |
| 5,830,341 A | 11/1998 | Gilmartin |
| 5,834,224 A | 11/1998 | Ruger et al. |
| 5,837,199 A | 11/1998 | Dumschat |
| 5,837,454 A | 11/1998 | Cozzette et al. |
| 5,842,983 A | 12/1998 | Abel et al. |
| 5,846,702 A | 12/1998 | Deng et al. |
| 5,846,744 A | 12/1998 | Athey et al. |
| 5,849,055 A | 12/1998 | Arai et al. |
| 5,857,983 A | 1/1999 | Douglas et al. |
| 5,873,990 A | 2/1999 | Wojciechowski et al. |
| 5,879,311 A | 3/1999 | Duchon et al. |
| 5,906,723 A | 5/1999 | Mathies et al. |
| 5,906,921 A | 5/1999 | Ikeda et al. |
| 5,942,102 A | 8/1999 | Hodges et al. |
| 5,951,492 A | 9/1999 | Douglas et al. |
| 5,951,493 A | 9/1999 | Douglas et al. |
| 5,951,836 A | 9/1999 | McAleer et al. |
| 5,954,643 A | 9/1999 | VanAntwerp et al. |
| 5,958,779 A | 9/1999 | Bonnick et al. |
| 5,971,941 A | 10/1999 | Simons et al. |
| 5,989,409 A | 11/1999 | Kurnik et al. |
| 5,997,708 A | 12/1999 | Craig |
| 5,997,817 A | 12/1999 | Crismore et al. |
| 6,004,441 A | 12/1999 | Fujiwara et al. |
| 6,022,366 A | 2/2000 | Schraga |
| 6,027,459 A | 2/2000 | Shain et al. |
| 6,032,059 A | 2/2000 | Henning et al. |
| 6,033,866 A | 3/2000 | Guo et al. |
| 6,036,924 A | 3/2000 | Simons et al. |
| 6,045,676 A | 4/2000 | Mathies et al. |
| 6,063,039 A | 5/2000 | Cunningham et al. |
| D427,312 S | 6/2000 | Douglas |
| 6,071,249 A | 6/2000 | Cunningham et al. |
| 6,071,251 A | 6/2000 | Cunningham et al. |
| 6,071,391 A | 6/2000 | Gotoh et al. |
| 6,093,156 A | 7/2000 | Cunningham et al. |
| 6,099,484 A | 8/2000 | Douglas et al. |
| 6,103,033 A | 8/2000 | Say et al. |
| 6,117,290 A | 9/2000 | Say et al. |
| 6,120,676 A | 9/2000 | Heller et al. |
| 6,129,823 A | 10/2000 | Hughes et al. |
| 6,129,843 A | 10/2000 | Petty et al. |
| 6,132,580 A | 10/2000 | Mathies et al. |
| 6,134,461 A | 10/2000 | Say et al. |
| 6,143,164 A | 11/2000 | Heller et al. |
| 6,156,051 A | 12/2000 | Schraga |
| 6,174,420 B1 | 1/2001 | Hodges et al. |
| 6,179,979 B1 | 1/2001 | Hodges et al. |
| 6,190,398 B1 | 2/2001 | Schraga |
| 6,192,891 B1 | 2/2001 | Gravel et al. |
| 6,206,841 B1 | 3/2001 | Cunningham et al. |
| 6,210,420 B1 | 4/2001 | Mauze et al. |
| 6,283,926 B1 | 9/2001 | Cunningham et al. |
| 6,283,982 B1 | 9/2001 | Levaughn et al. |
| 6,284,125 B1 | 9/2001 | Hodges et al. |
| 6,299,757 B1 | 10/2001 | Feldman et al. |
| 6,306,104 B1 | 10/2001 | Cunningham et al. |
| 6,306,152 B1 | 10/2001 | Verdonk et al. |
| 6,338,790 B1 | 1/2002 | Feldman et al. |
| 6,346,114 B1 | 2/2002 | Schraga |
| 6,352,514 B1 | 3/2002 | Douglas et al. |
| 6,368,141 B1 | 4/2002 | VanAntwerp et al. |
| 6,409,740 B1 | 6/2002 | Kuhr et al. |
| 6,436,255 B2 | 8/2002 | Yamamoto et al. |
| 6,444,115 B1 | 9/2002 | Hodges et al. |
| 6,461,496 B1 | 10/2002 | Feldman et al. |
| 6,475,360 B1 | 11/2002 | Hodges et al. |
| 6,506,168 B1 | 1/2003 | Fathallah et al. |
| 6,521,110 B1 | 2/2003 | Hodges et al. |
| 6,540,891 B1 | 4/2003 | Stewart et al. |
| 6,551,494 B1 | 4/2003 | Heller et al. |
| 6,576,101 B1 | 6/2003 | Heller et al. |
| 6,591,125 B1 | 7/2003 | Buse et al. |
| 6,592,745 B1 | 7/2003 | Feldman et al. |
| 6,592,815 B1 | 7/2003 | Zimmer |
| 6,599,407 B2 | 7/2003 | Taniike et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,630,415 B2 | 10/2003 | Phillips et al. |
| 6,632,349 B1 | 10/2003 | Hodges et al. |
| 6,740,215 B1 | 5/2004 | Nakaminami et al. |
| 6,749,740 B2 | 6/2004 | Liamos et al. |
| 6,764,581 B1 | 7/2004 | Forrow et al. |
| 6,793,633 B2 | 9/2004 | Douglas et al. |
| 6,863,800 B2 | 3/2005 | Karinka et al. |
| 6,863,801 B2 | 3/2005 | Hodges et al. |
| 6,878,251 B2 | 4/2005 | Hodges et al. |
| 6,885,196 B2 | 4/2005 | Taniike et al. |
| 6,939,450 B2 | 9/2005 | Karinka et al. |
| 6,942,518 B2 | 9/2005 | Liamos et al. |
| 7,058,437 B2 | 6/2006 | Buse et al. |
| 7,063,771 B2 | 6/2006 | Halabisky |
| 7,063,776 B2 | 6/2006 | Huang |
| 7,125,481 B2 | 10/2006 | Musho et al. |
| 7,335,294 B2 * | 2/2008 | Heller et al. .................. 205/792 |
| 7,348,183 B2 | 3/2008 | Fritsch et al. |
| 2003/0116447 A1 | 6/2003 | Wilsey |
| 2003/0143113 A2 | 7/2003 | Yuzhakov et al. |
| 2003/0155237 A1 | 8/2003 | Wilsey |
| 2004/0002682 A1 | 1/2004 | Kovelman et al. |
| 2004/0031682 A1 | 2/2004 | Wilsey |
| 2008/0277292 A1 | 11/2008 | Heller et al. |

FOREIGN PATENT DOCUMENTS

| | | |
|---|---|---|
| DE | 29720299 | 1/1998 |
| EP | 0470649 | 2/1992 |
| GB | 1318815 | 5/1973 |
| JP | 54-41191 | 4/1979 |
| JP | 55-10581 | 1/1980 |
| JP | 55-10583 | 1/1980 |
| JP | 55-10584 | 1/1980 |
| JP | 55-12406 | 1/1980 |
| JP | 56-163447 | 12/1981 |
| JP | 57-70448 | 4/1982 |

| | | |
|---|---|---|
| JP | 57-98853 | 6/1982 |
| JP | 58-211646 | 12/1983 |
| JP | 59-34882 | 2/1984 |
| JP | 59-67452 | 4/1984 |
| JP | 59-147249 | 8/1984 |
| JP | 60-173457 | 9/1985 |
| JP | 60-211350 | 10/1985 |
| JP | 62-139629 | 6/1987 |
| JP | 64-54345 | 3/1989 |
| JP | 1-114746 | 5/1989 |
| JP | 1-114747 | 5/1989 |
| JP | 1-124060 | 5/1989 |
| JP | 1-134244 | 5/1989 |
| JP | 1-1566658 | 6/1989 |
| JP | 01291153 | 11/1989 |
| JP | 2-62958 | 3/1990 |
| JP | 2-120655 | 5/1990 |
| JP | 2-245650 | 10/1990 |
| JP | 2-287145 | 11/1990 |
| JP | 2-310457 | 12/1990 |
| JP | 3-26956 | 2/1991 |
| JP | 3-28752 | 2/1991 |
| JP | 3-165249 | 7/1991 |
| JP | 3-202764 | 9/1991 |
| JP | 4-194660 A | 7/1992 |
| JP | 5-72171 | 3/1993 |
| JP | 05149910 | 6/1993 |
| JP | 5-196595 | 8/1993 |
| JP | 6-109688 | 4/1994 |
| JP | 06-130032 A | 5/1994 |
| JP | 7-27734 | 1/1995 |
| JP | 7-55757 A | 3/1995 |
| JP | 7-72585 | 3/1995 |
| JP | 8-285814 A | 11/1996 |
| JP | 8-285815 A | 11/1996 |
| JP | 8-320304 | 12/1996 |
| JP | 9-264870 | 10/1997 |
| JP | 10-170471 A | 6/1998 |
| WO | WO 95/22597 | 8/1995 |
| WO | WO 96/00614 A1 * | 1/1996 |
| WO | WO 9700441 A1 * | 1/1997 |
| WO | WO 98/35225 | 8/1998 |
| WO | WO 99/08106 | 2/1999 |

OTHER PUBLICATIONS

Bratten et al., "Micromachining Sensors for Electrochemical Measurement in Subnanoliter Volumes," Anal. Chem., vol. 69. (1997) pp. 253-258.
Cassidy et al., "Novel Electrochemical Device for the Detection of Cholesterol or Glucose" Analyst, Apr. 1993 vol. 118 pp. 415-418.
Daruhazi et al., "Cyclic Voltammetry for Reversible Redox-Electrode Reactions in Thin-Layer Cells with Closely Separated Working and Auxiliary Electrodes of the Same" J. Electroanal Chem. 264 (1989) 77-89.
Kissinger, "Biomedical Applications of Liquid Chromotography-Electrochemistry" Journal of Chromotography, 488 (1989) 31-52.
Karube et al., "Microbiosensors Prepared by Micromachining." GBF Monographs, vol. 17 (Biosens.: Fundam. Technol. Appl;.) (1992) 477-489.
Niwa et al., Concentration of Extracellular L-Glutamate Released from Cultured Nerve Cells Measured with a Small-Volume Online Sensor, Anal. Chem. vol. 68, (1996) pp. 1865-1870.
Takata, "Chapter 4-Liquid Chromatography with Coulometric Detector, "Methods on Chromotography—vol. 1: Advances in Liquid Chromatography, eds. Hanai & Hatano, World Scientific (1996).
Tietz, in: "Textbook of Clinical Chemistry", C.A. Burtis and E.R> Ashwood, eds., W.B. Saunders Co. Phila 1994, pp. 2210-2212.
Uhegbu et al., "Initial Studies of a New Approach to the Design and Use of Enzyme-Based Reactor/Sensor Systems: Amperometric System for Glucose" Anal. Chem. 1993, 65, 2443-2451.
Yang et al., "Application of "Wired" Peroxidase Electrodes for Peroxide Determination in Liquid Chromatography Coupled to Oxidase Immobilized Enzyme Reactors" Anal. Chem, 1995, 67, 1326-1331.
Yang et al., "Continuous Monitoring of Subcutaneous Glucose and Lactate Using Microdialysis with On-Line Enzyme Electrodes" Current Separations 14:1 (1995) pp. 31-35.

Bindra, D.S. et al., "Design and in Vitro Studies of a Needle-Type Glucose Sensor for Subcutaneous Monitoring", Anal. Chem., 63(17):1692-1696 (Sep. 1, 1991).
Bobbioni-Harsch, E. et al., "Lifespan of subcutaneous glucose sensors and their performances during dynamic glycaemia changes in rats," J. Biomed. Eng. 15:457-463 (1993).
Bowyer et al., "Electrochemical Measurements in Submicroliter Volumes", Analytical Chemistry, 64, pp. 459-462 (1992).
Brandt, J. et al., "Covalent attachment of proteins to polysaccharide carriers by means of benzoquinone," Biochim. Biophys. Acta, 386(1) (1 page Abstract only) (1975).
Brownlee, M. et al., "A Glucose-Controlled Insulin-Delivery System: Semisynthetic Insulin Bound to Lectin", Science, 206(4423):1190-1191 (Dec. 7, 1979).
Cass, A.E.G. et al., "Ferrocene-Mediated Enzyme Electrode for Amperometric Determination of Glucose", Anal. Chem., 56(4):667-671 (Apr. 1984).
Cass, A.E.G. et al., "Ferricinum Ion As an Electron Acceptor for Oxido-Reductases," J. Electroanal. Chem., 190:117-127 (1985).
Castner, J. F. et al., "Mass Transport and Reaction Kinetic Parameters Determined Electrochemically for Immobilized Glucose Oxidase," Biochemisty, 23(10):2203-2210 (1984).
Claremont, D.J. et al., "Biosensors for Continuous in Vivo Glucose Monitoring", IEEE Engineering in Medicine and Biology Society 10th Annual International Conference, New Orleans, Louisiana, 3 pp. (Nov. 4-7, 1988).
Clark, L.C. et al., "Differential Anodic Enzyme Polarography for the Measurement of Glucose", Oxygen Transport to Tissue: Instrumentation, Methods, and Physiology, 127-133 (1973).
Clark, L.C. et al., "Long-term Stability of Electroenzymatic Glucose Sensors Implanted in Mice," Trans. Am. Soc. Artif. Intern. Organs, XXXIV:259-265 (1988).
Clarke, W. L., et al., "Evaluating Clinical Accuracy of Systems for Self-Monitoring of Blood Glucose," Diabetes Care, 10(5):622-628 (Sep.-Oct. 1987).
Csoregi, E. et al., "Design, Characterization, and One-Point in Vivo Calibration of a Subcutaneously Implanted Glucose Electrode," Anal. Chem. 66(19):3131-3138 (Oct. 1, 1994).
Csoregi, E. et al., "On-Line Glucose Monitoring by Using Microdialysis Sampling and Amperometric Detection Based on "Wired" Glucose Oxidase in Carbon Paste," Mikrochim. Acta. 121:31-40 (1995).
Csoregi, E. et al., "Design and Optimization of a Selective Subcutaneously Implantable Glucose Electrode Based on "Wired" Glucose Oxidase," Anal. Chem. 67(7):1240-1244 (Apr. 1, 1995).
Davis, G., "Electrochemical Techniques for the Development of Amperometric Biosensors", Biosensors, 1:161-178 (1985).
Degani, Y. et al., "Direct Electrical Communication between Chemically Modified Enzymes and Metal Electrodes. 1. Electron Transfer from Glucose Oxidase to Metal Electrodes via Electron Relays, Bound Covalently to the Enzyme," J. Phys. Chem., 91(6):1285-1289 (1987).
Degani, Y. et al., "Direct Electrical Communication between Chemically Modified Enzymes and Metal Electrodes. 2. Methods for Bonding Electron-Transfer Relays to Glucose Oxidase and D-Amino-Acid Oxidase," J. Am. Chem. Soc., 110(8):2615-2620 (1988).
Degani, Y. et al., "Electrical Communication between Redox Centers of Glucose Oxidase and Electrodes via Electrostatically and Covalently Bound Redox Polymers," J. Am. Chem. Soc., 111:2357-2358 (1989).
Denisevich, P. et al., "Unidirectional Current Flow and Charge State Trapping at Redox Polymer Interfaces on Bilayer Electrodes: Principles, Experimental Demonstration, and Theory," J. Am. Chem. Soc., 103(16):4727-4737 (1981).
Dicks, J. M., "Ferrocene modified polypyrrole with immobilised glucose oxidase and its application in amperometric glucose microbiosensors," Ann. Biol. clin., 47:607-619 (1989).
Ellis, C. D., "Selectivity and Directed Charge Transfer through an Electroactive Metallopolymer Film," J. Am. Chem. Soc., 103(25):7480-7483 (1981).
Engstrom, R.C., "Electrochemical Pretreatment of Glassy Carbon Electrodes", Anal. Chem., 54(13):2310-2314 (Nov. 1982).

Engstrom, R.C. et al., "Characterization of Electrochemically Pretreated Glassy Carbon Electrodes", Anal. Chem., 56(2):136-141 (Feb. 1984).

Enthone Inc., "ENPLATE DSR-3241 Cost and Process Control: Application Process," Imaging Technologies Update. Jun. 2001, No. 3.

Feldman, B.J. et al., "Electron Transfer Kinetics at Redox Polymer/Solution Interfaces Using Microelectrodes and Twin Electrode Thin Layer Cells", J. Electroanal. Chem., 194(1):63-81 (Oct. 10, 1985).

Fischer, H. et al., "Intramolecular Electron Transfer Mediated by 4,4'-Bipyridine and Related Bridging Groups", J. Am. Chem. Soc., 98(18):5512-5517 (Sep. 1, 1976).

Foulds, N. C. et al., "Enzyme Entrapment in Electrically Conducting Polymers," J. Chem. Soc., Faraday Trans 1., 82:1259-1264 (1986).

Foulds, N. C. et al., "Immobilization of Glucose Oxidase in Ferrocene-Modified Pyrrole Polymers," Anal. Chem., 609(22):2473-2478 (Nov. 15, 1988).

Frew, J.E. et al., "Electron-Transfer Biosensors", Phil. Trans. R. Soc. Lond., B316:95-106 (1987).

Gamache et al. ("Simultaneous measurement of monamines, metabolites and amino acids in brain tissue and microdialysis perfusates", J. Chromatogr., Biomed. Appl. (1993), 614(2), 213-20), 1993.

Gorton, L. et al., "Selective detection in flow analysis based on the combination of immobilized enzymes and chemically modified electrodes," Analytica Chimica Acta., 250:203-248 (1991).

Gregg, B. A. et al., "Cross-Linked Redox Gels Containing Glucose Oxidase for Amperometric Biosensor Applications," Analytical Chemistry, 62(3):258-263 (Feb. 1, 1990).

Gregg, B. A. et al., "Redox Polymer Films Containing Enzymes. 1. A Redox-Conducting Epoxy Cement: Sythesis, Characterization, and Electrocatalytic Oxidation of Hydroquinone," J. Phys. Chem., 95(15):5970-5975 (1991).

Grubb et al., "Blood oxygen content in microliter samples using an easy-to-build galvanic cell", Journal of Applied Physiology, pp. 456-464 (1981).

Hale, P.D. et al., "A New Class of Amperometric Biosensor Incorporating a Polymeric Electron-Transfer Mediator," J. Am. Chem. Soc., 111(9):3482-3484 (1989).

Harrison, D.J. et al., "Characterization of Perfluorosulfonic Acid Polymer Coated Enzyme Electrodes and a Miniaturized Integrated Potentiostat for Glucose Analysis in Whole Blood", Anal. Chem., 60(19):2002-2007 (Oct. 1, 1988).

Hawkridge, F. M. et al., "Indirect Coulometric Titration of Biological Electron Transport Components," Analytical Chemistry, 45(7):1021-1027 (Jun. 1973).

Heineman, W.R. "Spectro-electro-chemistry", Analytical Chemistry, 50(3):390-392, 394, 396, 398, 400, 402 (Mar. 1978).

Heineman, W.R. et al., "Measurement of Enzyme E.degree. Values by Optically Transparent Thin Layer Electrochemical Cells", Analytical Chemistry, 47(1):79, 82-84 (Jan. 1975).

Heller, A., "Electrical Wiring of Redox Enzymes," Acc. Chem. Res., 23(5):129-134 (1990).

Heller, A., "Electrical Connection of Enzyme Redox Centers to Electrodes," J. Phys. Chem 96(9):3579-3587 (1992).

Heller, A., "Amperometric biosensors based on three-dimensional hydrogel-forming epoxy networks," Sensors and Actuators B, 13-14:180-183 (1993).

Hubbard, A. et al. "The Theory and Practice of Electrochemistry with Thin Layer Cells", Electroanalytical Chemistry A Series of Advances, vol. 4, pp. 129-131, 142-147, 168-171, edited by Allen J. Bard, Marcel Deckker, Inc. New York (1970).

Hubbard, A. et al., "Electrochemistry in Thin Layers of Solution", CRC Critical Reviews in Analytical Chemistry, 3(2):201-242 (Mar. 1973).

Ianniello, R.M. et al., "Differential Pulse Voltammetric Study of Direct Electron Transfer in Glucose Oxidase Chemically Modified Graphite Electrodes", Anal. Chem., 54:(7):1098-1101 (Jun. 1981).

Ianniello, R.M. et al. "Immobilized Enzyme Chemically Modified Electrode as an Amperometric Sensor", Anal. Chem., 53(13):2090-2095 (Nov. 1981).

Ikeda, T. et al., "Glucose oxidase-immobilized benzoquinone-carbon paste electrode as a glucose sensor," Agric. Biol. Chem., 49(2) (1 page—Abstract only) (1985).

Ikeda, T. et al., "Kinetics of Outer-Sphere Electon Transfers Between Metal Complexes in Solutions and Polymeric Films on Modified Electrodes", J. Am. Chem. Soc., 103(25):7422-7425 (Dec. 16, 1981).

Johnson, J. M. et al., "Potential-Dependent Enzymatic Activity in a Enzyme Thin-Layer Cell," Anal. Chem. 54:1377-1383 (1982).

Johnson, K.W., "Reproducible Electrodeposition of Biomolecules for the Fabrication of Miniature Electroenzymatic Biosensors", Sensors and Actuators B Chemical, B5:85-89 (1991).

Jonsson, G. et al., "An Amperometric Glucose Sensor Made by Modification of a Graphite Electrode Surface With Immobilized Glucose Oxidase and Adsorbed Mediator", Biosensors, 1:35-368 (1985).

Josowicz, M. et al., "Electrochemical Pretreatment of Thin Film Platinum Electrodes", J. Elecrochem. Soc., 135(1):112-115 (Jan. 1988).

Katakis, I. et al., "L-.alpha.-Glycerophosphate and L-Lactate Electrodes Based on the Electrochemical "Wiring" of Oxidases," Analytical Chemistry, 64(9):1008-1013 (May 1, 1992).

Katakis, I. et al., "Electrostatic Control of the Electron Transfer Enabling Binding of Recombinant Glucose Oxidase and Redox Polyelectrolytes," J. Am. Chem. Soc., 116(8):3617-3618 (1994).

Kenausis, G. et al., "Wiring of glucose oxidase and lactate oxidase within a hydrogel made with poly(vinyl pyridine) complexed with [Os(4,4'-dimethoxy-2,2'-bipyridine).sub.2 C1].sup.+/2+," J. Chem. Soc., Faraday Trans., 92(20):4131-4136 (1996).

Koudelka, M. et al., "In-Vivo Behaviour of Hypodermically Implanted Microfabricated Glucose Sensors", Biosensors & Bioelectronics, 6(1):31-36 (1991).

Kulys, J. et al., "Mediatorless peroxidase electrode and preparation of bienzyme sensors," Bioelectrochemistry and Bioenergetics, 24:305-311 (1990).

Lager, W. et al., "Implantable Electrocatalytic Glucose Sensor," Horm. Metab. Res., 26:526-530 (Nov. 1994).

Lindner, E. et al. "Flexible (Kapton-Based) Microsensor Arrays of High Stability for Cardiovascular Applications", J. Chem. Soc. Faraday Trans., 89(2):361-367 (Jan. 21, 1993).

Maidan, R. et al., "Elimination of Electrooxidizable Interferant-Produced Currents in Amperometric Biosensros," Analytical Chemistry, 64(23):2889-2896 (Dec. 1, 1992).

McNeil, C. J. et al., "Thermostable Reduced Nicotinamide Adenine Dinucleotide Oxidase: Application to Amperometric Enzyme Assay," Anal. Chem., 61(1):25-29 (Jan. 1, 1989).

Miyawaki, O. et al., "Electrochemical and Glucose Oxidase Coenzyme Activity of Flavin Adenine Dinucleotide Covalently Attached to Glass Carbon at the Adenine Amino Group", Biochimica et Biophysica Acta, 838:60-68 (1985).

Moatti-Sirat, D. et al., "Evaluating in vitro and in vivo the inteference of ascorbate and acetaminophen on glucose detection by a needle-type glucose sensor," Biosensors & Bioelectronics, 7(5):345-352 (1992).

Moatti-Sirat, D. et al., "Towards continuous glucose monitoring: in vivo evaluation of a miniaturized glucose monitoring: in vivo evaluation of a miniaturized glucose sensor implanted for several days in rat subcutaneous tissue," Diabetologia, 35(3) (1 page—Abstract only) (Mar. 1992).

Moatti-Sirat, D. et al., "Reduction of acetaminophen interference in glucose sensors by a composite Nafion membrane: demostration in rats and man," Diabetologia, 37(6) (1 page—Abstract only) (Jun. 1994).

Morris, N.A., "An electrochemical Capillary Fill Device for the Analysis of Glucose Incorporating Glucose Oxidase and Ruthenium (III) Heamine as Mediator," Electroanalysis, vol. 4, No. 1 (Jan. 1992).

Nakamura, S. et al., "Effect of Periodate Oxidation on the Structure and Properties of Glucose Oxidase," Biochimica et Biophysica Acta., 445:294-308 (1976).

Narazimhan, K. et al., "p-Benzoquinone activation of metal oxide electrodes for attachment of enzymes," Enzyme Microb. Technol., 7(6) (1 page—Abstract only) (1985).

Ohara, T. J. et al., "'Wired' Enzyme Electrodes for Amperometric Determination of Glucose or Lactate in the Presence of Interfering Substances," Analytical Chemistry, 66(15):2451-2457 (Aug. 1, 1994).

Ohara, T. J., "Osmium Bipyridyl Redox Polymers Used in Enzyme Electrodes," Platinum Metals Rev., 39(2):54-62 (Apr. 1995).

Olievier, C. N. et al., "In vivo Measurement of Carbon Dioxide Tension with a Miniature Electrode," Pflugers Arch. 373:269-272 (1978).

Paddock, R. et al., "Electrocatalytic reduction of hydrogen peroxide via direct electron transfer from pyrolytic graphite electrodes to irreversibly adsorbed cytochrome c peroxidase," J. Electroanal. Chem., 260:487-494 (1989).

Palleschi, G. et al., "A Study of Interferences in Glucose Measurements in Blood by Hydrogen Peroxide Based Glucose Probes", Anal. Biochem., 159:114-121 (1986).

Pickup, J. et al., "Potentially-implantable amperometric glucose sensors with mediated electron transfer: improving the operating stability," Biosensors, 4(2) (1 page—Abstract only) (1989).

Pickup, J. C. et al., "In vivo molecular sensing in diabetes mellitus: an implantable glucose sensor with direct electron transfer," Diabetologia, 32(3):213-217 (1989).

Pickup, J., "Developing glucose sensors for in vivo use," TIBTECH, 11(7): 285-289 (Jul. 1993).

Pishko, M.V. et al., "Amperometric Glucose Microelectrodes Prepared Through Immobilization of Glucose Oxidase in Redox Hydrogels", Anal. Chem., 63(20):2268-2272 (Oct. 15, 1991).

Poitout, V. et al., "In vitro and in vivo evaluation in dogs of a miniaturized glucose sensor," ASAIO Transactions, 37(3) (1 page—Abstract only) (Jul.-Sep. 1991).

Poitout, V. et al., "Calibration in dogs of a subcutaneous miniaturized glucose sensor using a glucose meter for blood glucose determination," Biosensors & Bioelectronics, 7:587-592 (1992).

Poitout, V. et al., "A glucose monitoring system for on line estimation in man of blood glucose concentration using a miniaturized glucose sensor implanted in the subcutaneous tissue and a wearable control unit," Diabetolgia, 36(7) (1 page—Abstract only) (Jul. 1993).

Pollak, A. et al., "Enzyme Immobilization by Condensation Copolymerization into Cross-Linked Polyacrylamide Gels," J. Am. Chem. Soc., 102(20):6324-6336 (1980).

Reach, G. et al., "Can Continuous Glucose Monitoring Be Used for the Treatment of Diabetes?" Analytical Chemistry, 64(6):381-386 (Mar. 15, 1992).

Rebrin, K. et al., "Automated Feedback Control of Subcutaneous Glucose Concentration in Diabetic Dogs", Diabetologia, 32(8):573-576 (Aug. 1989).

Roche's Final Invalidity Contentions of '745 and '551 Patents as of Jun. 18, 2007, and references.

Roe, "Comparison of Amperometric and Coulometric Electrochemical Detectors for HPLC through a Figure of Merit", Analytical Letters, 16(A8), 613-631 (1983).

Sakakida, M. et al., "Ferrocene-mediate needle-type glucose sensor covered with newly designed biocompatible membrane," Sensors and Actuators .beta., 13-14:319-322 (1993).

Sasso, S.V. et al., "Electropolymerized 1,2-Diaminobenzene as a Means to Prevent Interferences and Fouling and to Stabilize Immobilized Enzyme in Electrochemical Biosensors", Anal. Chem., 62(11): 1111-1117 (Jun. 1, 1990).

Schmehl, R.H. et al., "The Effect of Redox Site Concentration on the Rate of Mediated Oxidation of Solution Substrates by a Redox Copolymer Film", J. Electroanal. Chem., 152:97-109 (Aug. 25, 1983).

Shichiri, M. et al., "Glycemic Control in Pancreatectomized Dogs with a Wearable Artificial Endocrine Pancreas", Diabetologia, 24(3):179-184 (Mar. 1983).

Sittampalam, G. et al., "Surface-Modified Electrochemical Detector for Liquid Chromatography", Anal. Chem., 55(9):1608-1610 (Aug. 1983).

Sprules, S. D. et al., "Evaluation of a New Disposable Screen-Printed Sensor Strip for the Measurement of NADH and Its Modification to Produce a Lactate Biosensor Employing Microliter Volumes," Electroanalysis, 8(6):539-543 (1996).

Sternberg, R. et al., "Study and Development of Multilayer Needle-type Enzyme-based Glucose Microsensors," Biosensors, 4:27-40 (1988).

Sternberg, R. et al., "Covalent Enzyme Coupling on Cellulose Acetate Membranes for Glucose Sensor Development," Analytical Chemistry, 60(24):2781-2786 (Dec. 15, 1988).

Sternberg, F. et al., "Calibration Problems of Subcutaneous Glucosensors when Applied "In-Situ" in Man," Horm. metabl. Res, 26:523-525 (1994).

Suekane, M., "Immobilization of glucose isomerase," Zeitschrift fur Allgemeine Mikrobiologie, 22(8):565-576 (1982).

Tajima, S. et al., "Simultaneous Determination of Glucose and 1.5-Anydrogluc.sub.-- tol", Chemical Abstracts, 111(25):394 111:228556g (Dec. 18, 1989).

Tarasevich, M.R. "Bioelectrocatalysis", Comprehensive Treatise of Electrochemistry, 10 (Ch. 4):231-295 (1985).

Tatsuma, T. et al., "Enzyme Monolayer- and Bilayer-Modified Tin Oxide Electrodes for the Determination of Hydrogen Peroxide and Glucose," Anal. Chem., 61(2):2352-2355 (Nov. 1, 1989).

Taylor, C. et al., "'Wiring' of glucose oxidase within a hydrogel made with polyvinyl imidazole complexed with [(Os-4,4'-dimethoxy-2,2'-bipyridine)C1].sup.+/2+," Journal of Electroanalytical Chemistry, 396:511-515 (1995).

*Therasense, Inc.* (*now known as Abbott Diabetes Care Inc.*) *and Abbott Laboratories* v. *Becton, Dickinson and Company and Nova Biomedical Corporation, and Bayer Healthcare LLC*, United States Court of Appeals for the Federal Circuit, Decided: Jan. 25, 2010.

Trojanowicz, M. et al., "Enzyme Entrapped Polypyrrole Modified Electrode for Flow-Injection Determination of Glucose," Biosensors & Bioelectronics, 5:149-156 (1990).

Turner, A.P.F. et al., "Diabetes Mellitus: Biosensors for Research and Management", Biosensors, 1:85-115 (1985).

Turner, R. F. B. et al., "A Biocompatible Enzyme Electrode for Continuous in vivo Glucose Monitoring in Whole Blood," Sensors and Actuators, B1(1-6):561-564 (Jan. 1990).

Tuzhi, P. et al., "Constant Potential Pretreatment of Carbon Fiber Electrodes for in Vivo Electrochemistry", Analytical Letters, 24(6):935-945 (1991).

Umaha, M., "Protein-Modified Electrochemically Active Biomaterial Surface," U.S. Army Research Office Report, (12 pages) (Dec. 1988).

Urban, G. et al., "Miniaturized Thin-Film Biosensors Using Covalently Immobilized Glucose Oxidase", Biosensors & Bioelectronics, 6(7):555-562 (1991).

Van Der Schoot et al., "An ISFET-Based Microlite Titrator: Integration of a Chemical Sensor-Actuator System", Sensors and Actuators, 8:11-22 (1985).

Velho, G. et al., "In Vitro and In Vivo Stability of Electrode Potentials in Needle-Type Glucose Sensors", Diabetes, 38(2):164-171 (Feb. 1989).

Velho, G. et al., "Strategies for calibrating a subcutaneous glucose sensor," Biomed. Biochin. Acta, 48(11/12):957-964 (1989).

Von Woedtke, T. et al., "In Situ Calibration of Implanted Electrochemical Glucose Sensors," Biomed. Biochim. Acta, 48(11/12):943-952 (1989).

Vreeke, M. et al., "Hydrogen Peroxide and .beta.-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network," Analytical Chemistry, 64(24):3084-3090 (Dec. 15, 1992).

Vreeke, M. S. et al., "Chapter 15: Hydrogen Peroxide Electrodes Based on Electrical Connection of Redox Centers of Various Peroxidases to Electrodes through a Three-Dimensional Electron Relaying Polymer Network," Diagnostic Biosensor Polymers, 7 pp. (Jul. 26, 1993).

Vriend, J., "Determination of Amino Acids and Monoamine Neurotransmitters in Caudate Nucleus of Seizure-Resistant and Seizure-Prone BALB/c Mice," Journal of Neurochemistry, vol. 60, No. 4, pp. 1300-1307 (1993).

Wang, J. et al., "Activation of Glassy Carbon Electrodes by Alternating Current Electrochemical Treatment", Analytica Chimica Acta, 167:325-334 (Jan. 1985).

Wang, J. et al., "Amperometric biosensing of organic peroxides with peroxidase-modified electrodes," Analytica Chimica Acta. 254:81-88 (1991).

Wang, J. et al., "Screen-Printable Sol-Gel Enzyme-Containing Carbon Inks," Analytical Chemistry, 68(15):2705-2708 (Aug. 1, 1996).

Wang, J. et al., "Sol-Gel-Derived Metal-Dispersed Carbon Composite Amperometric Biosensors," Electroanalysis, 9(1):52-55 (1997).

Williams, D.L. et al., "Electrochemical-Enzymatic Analysis of Blood Glucose and Lactate", Anal. Chem., 42(1):118-121 (Jan. 1970).

Wilson, G. S. et al., "Progress toward the Development of an Implantable Sensor for Glucose," Clinical Chemistry, 38(9):1613-1617 (1992).

Yabuki, S. et al., "Electro-conductive Enzyme Membrane," J. Chem. Soc. Chem. Commun, 945-946 (1989).

Yang, L. et al., "Determination of Oxidase Enzyme Substrates Using Cross-Flow Thin-Layer Amperometry," Electroanalysis, 8(8-9):716-721 (1996).

Yao, S.J. et al., "The Interference of Ascorbate and Urea in Low-Potential Electrochemical Glucose Sensing", Proceedings of the Twelfth Annual International Conference of the IEEE Engineering in Medicine and Biology Society, 12(2):487-489 (Nov. 1-4, 1990).

Ye, L. et al., "High Current Density "Wired" Quinoprotein Glucose Dehydrogenase Electrode," Anal. Chem., 65(3):238-241 (Feb. 1, 1993).

Yildiz, A., "Evaluation of an Improved Thin-Layer Electrode", Analytical Chemistry, 40(7):1018-1024 (Jun. 1968).

Zamzow, K. et al., New Wearable Continuous Blood Glucose Monitor (BGM) and Artificial Pancreas (AP), Diabetes, 39:5A(20) (May 1990).

Zhang, Y. et al. "Application of cell culture toxicity tests to the development of implantable biosensors," Biosensors & Bioelectronics, 6:653-661(1991).

Pravda, M. et al., "Evaluation of amperometric glucose biosensors based on co-immobilisation of glucose oxidase with an osmium redox polymer in electrochemically generated polyphenol films," Analytica Chimica Acta, 304:127-138 (1995).

*TheraSense, Inc., v. Becton, Dickinson and Co.*, 560 F. Supp. 2d 835—Dist. Court, ND California (Apr. 3, 2008).

Batchelor et al., "Amperometric Assay for the Ketone body 3-Hydroxybutyrate," Analytica Chimica Acta, 221:289-294 (1989).

Choleau et al., "Calibration of a subcutaneous amperometric glucose sensor Part 1. Effect of measurement uncertainties on the determination of sensor sensitivity and background current," Biosensors and Bioelectronics, 17:641-646 (2002).

Kerner et al., "The function of a hydrogen peroxide-detecting electroenzymatic glucose electrode is markedly impaired in human sub-cutaneous tissue and plasma," Biosensors & Bioelectronics, 8:473-482 (1993).

Linke et al., "Prevention of the Decrease in Sensitivity of an Amperometric Glucose Sensor in Undiluted Human Serum," Clinical Chemistry, 45( 2):283-285 (1999).

Pickup et al., "Responses and calibration of amperometric glucose sensors implanted in the subcutaneous tissue of man," Acta. Diabetol., 30:143-148 (1993).

Thomé—Duret et al., "Modification of the Sensitivity of Glucose Sensor Implanted into Subcutaneous Tissue," Diabetes & Metabolism (Paris), 22:174-1 78 (1996).

Ward et al., "A new amperometric glucose microsensor: in vitro and short-term in vivo evaluation," Biosensors & Bioelectronics, 17:181-189 (2002).

Unwin et al., "A Generally Applicable Method for the Measurement of Heterogeneous Rate Constants of Reactions Occurring at the Solid/Liquid Interface," Journal of Colloid and Interface Science, 128(1):208-222 (Mar. 1989).

Diffusion coefficient of glucose in water—*Homo sapiens* from the Catalog of useful Biological Numbers at harvard.edu downloaded from http://bionumbers.hms.harvard.edu/ on Nov. 30, 2011.

* cited by examiner

SMALL VOLUME IN VITRO ANALYTE SENSOR

This application is a continuation of U.S. application Ser. No. 11/035,131, filed Jan. 13, 2005, which is a divisional of application Ser. No. 10/457,585, filed Jun. 9, 2003, which is a continuation of application Ser. No. 09/413,735, filed on Oct. 6, 1999, now U.S. Pat. No. 6,576,101, which is a divisional of application Ser. No. 08/795,767, filed Feb. 6, 1997 (now abandoned), all of which are incorporated by reference.

FIELD OF THE INVENTION

This invention relates to analytical sensors for the detection of bioanalytes in a small volume sample.

BACKGROUND OF THE INVENTION

Analytical sensors are useful in chemistry and medicine to determine the presence and concentration of a biological analyte. Such sensors are needed, for example, to monitor glucose in diabetic patients and lactate during critical care events.

Currently available technology measures bioanalytes in relatively large sample volumes, e.g., generally requiring 3 microliters or more of blood or other biological fluid. These fluid samples are obtained from a patient, for example, using a needle and syringe, or by lancing a portion of the skin such as the fingertip and "milking" the area to obtain a useful sample volume. These procedures are inconvenient for the patient, and often painful, particularly when frequent samples are required. Less painful methods for obtaining a sample are known such as lancing the arm or thigh, which have a lower nerve ending density. However, lancing the body in the preferred regions typically produces submicroliter samples of blood, because these regions are not heavily supplied with near-surface capillary vessels.

It would therefore be desirable and very useful to develop a relatively painless, easy to use blood analyte sensor, capable of performing an accurate and sensitive analysis of the concentration of analytes in a small volume of sample.

SUMMARY OF THE INVENTION

The sensors of the present invention provide a method for the detection and quantification of an analyte in submicroliter samples. In general, the invention includes a method and sensor for analysis of an analyte in a small volume of sample, preferably by coulometry. A biosensor of the invention utilizes a non-leachable redox mediator, preferably an air-oxidizable redox mediator, and preferably immobilized on a working electrode. The biosensor also includes a sample chamber to hold the sample in electrolytic contact with the working electrode. In a preferred embodiment, the working electrode faces a counter electrode, forming a measurement zone within the sample chamber, between the two electrodes, that is sized to contain less than about 1 µL of sample, preferably less than about 0.5 µL, more preferably less than about 0.2 µL, and most preferably less than about 0.1 µL of sample. A sorbent material is optionally positioned in the sample chamber and measurement zone to reduce the volume of sample needed to fill the sample chamber and measurement zone.

In one embodiment of the invention, a biosensor is provided which combines the efficiency of coulometric electrochemical sensing with a non-leachable redox mediator to accurately and efficiently measure a bioanalyte in a submicroliter volume of sample. The preferred sensor includes an electrode, a non-leachable redox mediator on the electrode, a sample chamber for holding the sample in electrical contact with the electrode and, preferably, sorbent material disposed within the sample chamber to reduce the volume of the chamber. The sample chamber, together with any sorbent material, is sized to provide for analysis of a sample volume that is typically less than about 1 µL, preferably less than about 0.5 µL, more preferably less than about 0.2 µL, and most preferably less than about 0.1 µL.

One embodiment of the invention includes a method for determining the concentration of an analyte in a sample by, first, contacting the sample with an electrochemical sensor and then determining the concentration of the analyte. The electrochemical sensor includes a facing electrode pair with a working electrode and a counter electrode and a sample chamber, including a measurement zone, positioned between the two electrodes. The measurement zone is sized to contain less than about 1 µL of sample.

The invention also includes an electrochemical sensor with two or more facing electrode pairs. Each electrode pair has a working electrode, a counter electrode, and a measurement zone between the two electrodes, the measurement zone being sized to hold less than about 1 µL of sample. In addition, the sensor also includes non-leachable redox mediator on the working electrode of at least one of the electrode pairs.

One aspect of the invention is a method of determining the concentration of an analyte in a sample by contacting the sample with an electrochemical sensor and determining the concentration of the analyte by coulometry. The electrochemical sensor includes an electrode pair with a working electrode and a counter electrode. The sensor also includes a sample chamber for holding a sample in electrolytic contact with the working electrode. Within the sample chamber is sorbent material to reduce the volume sample needed to fill the sample chamber so that the sample chamber is sized to contain less than about 1 µL of sample.

The invention also includes a sensor and a method for the determination of the concentration of an analyte in a sample having a volume of less than about 1 µL. The sensor has a support and an air-oxidizable redox mediator coated on the support. At least 90% of the air-oxidizable redox mediator is in an oxidized state prior to introduction of a sample. The method includes contacting the sample with the sensor and correlating the concentration of the analyte in the sample to a change in oxidation state of the redox mediator in the presence of the sample. The sensor and method of this aspect of the invention are directed to, but not limited to, electrochemical and optical sensors.

A further aspect of the invention is an integrated sample acquisition and analyte measurement device which includes a sample acquisition means for producing a patient sample as well as a sensor of the invention for measuring analyte in the sample. The device is used for measuring analyte in a patient sample by, first, contacting the patient with the device and then determining the concentration of the analyte, preferably by coulometry.

Another aspect of the invention is a method for determining the concentration of an analyte in the sample with reduced error by contacting the sample with an electrochemical sensor that includes a first and a second electrode pair. Each electrode pair has a working electrode and a sample chamber for holding the sample in electrolytic contact with the working electrode, the sample chamber being sized to contain less than about 1 µL of sample. The first electrode pair also has a non-leachable redox mediator and non-leachable enzyme on the working electrode. The second electrode pair has a non-leachable redox mediator in the absence of enzyme on the working electrode. The method further includes the step of measuring substantially simultaneously, and at two or more times, a first current generated at the first electrode pair and a second current generated at the second electrode pair. The measured first currents and second currents are independently integrated to give a first charge and a second charge, respectively. The second charge is subtracted from the first charge to give a noise-reduced charge which is then correlated to the concentration of analyte in the sample. This method can be used to remove errors arising from interferents or the mixed oxidation state of the redox mediator prior to introduction of the sample.

Another method of the invention for the determination of the concentration of an analyte in a sample includes the step of providing an electrochemical sensor which has one or more facing electrode pairs, each pair having a working and a counter electrode and a measurement zone between the working and counter electrodes, the measurement zones of the one or more electrode pairs having approximately equal volumes of less than about 1 µL. The sensor also includes redox mediator on the working electrode of at least one of the electrode pairs. The method further includes measuring a capacitance of one of the electrode pairs and calculating the volume of the measurement zone of that electrode pair from the capacitance measurement. In addition, the sensor is brought into contact with the sample and the concentration of analyte in the sample is determined by coulometry.

A further aspect of the invention is a method of storing and packaging an analytical sensor which includes packaging the sensor in an atmosphere containing molecular oxygen. The sensor of this aspect of the invention includes air-oxidizable redox mediator.

One embodiment of the invention is a method of determining the concentration of an analyte in a sample by contacting the sample with an electrochemical sensor, electrolyzing less than about 1 µL of sample, and determining the concentration of the analyte by coulometry. The sensor of this embodiment of the invention includes a working electrode and non-leachable redox mediator on the working electrode. The molar amount of non-leachable redox mediator in the reduced form prior to introduction of the sample into the sensor is less than, on a stoichiometric basis, 5% of the expected molar amount of analyte to be electrolyzed.

Another method for determining the concentration of an analyte in a sample includes contacting the sample with an electrochemical sensor which has a working electrode, a counter electrode, and a measurement zone bounded on at least two sides by the two electrodes. The measurement zone is sized to contain less than about 1 µL of sample. The concentration of analyte in the sample is then determined by coulometry.

These and various other features which characterize the invention are pointed out with particularity in the attached claims. For a better understanding of the invention, its advantages, and objectives obtained by its use, reference should be made to the drawings and to the accompanying description, in which there is illustrated and described preferred embodiments of the invention.

BRIEF DESCRIPTION OF THE DRAWINGS

Referring now to the drawings, wherein like reference numerals and letters indicate corresponding structure throughout the several views.

DETAILED DESCRIPTION OF THE PREFERRED EMBODIMENT

Figure 1:
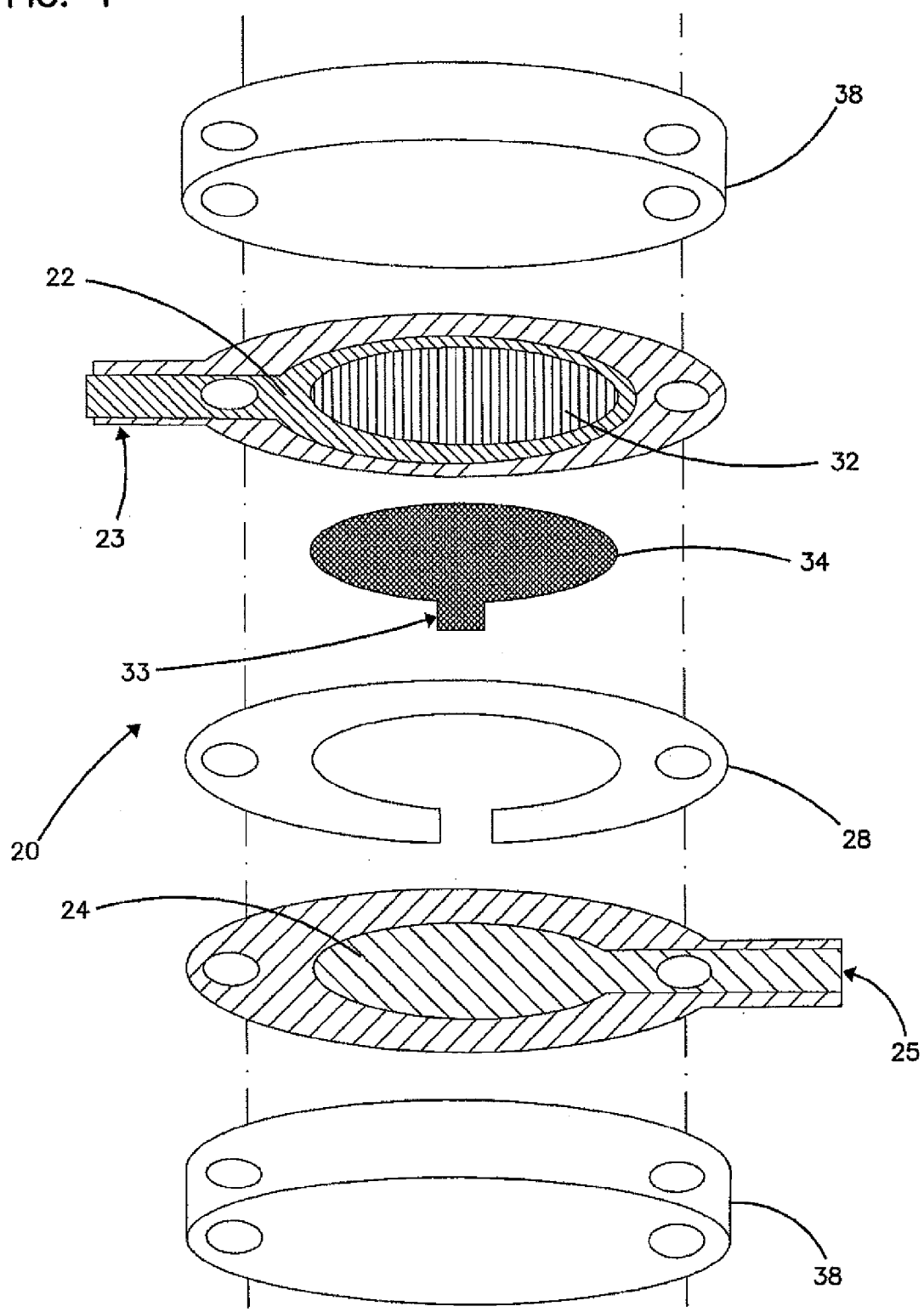
FIG. 1 is a schematic view of a first embodiment of an electrochemical sensor in accordance with the principles of the present invention having a working electrode and a counter electrode facing each other.

When used herein, the following definitions define the stated term:

An "air-oxidizable mediator" is a redox mediator that is oxidized by air, preferably so that at least 90% of the mediator is in an oxidized state upon storage in air within a useful period of time, e.g., one month or less, and, preferably, one week or less, and, more preferably, one day or less.

A "biological fluid" is any body fluid in which the analyte can be measured, for example, blood, interstitial fluid, dermal fluid, sweat, and tears.

The term "blood" in the context of the invention includes whole blood and its cell-free components, namely, plasma and serum.

"Coulometry" is the determination of charge passed or projected to pass during complete or nearly complete electrolysis of the analyte, either directly on the electrode or through one or more electron transfer agents. The charge is determined by measurement of charge passed during partial or nearly complete electrolysis of the analyte or, more often, by multiple measurements during the electrolysis of a decaying current and elapsed time. The decaying current results from the decline in the concentration of the electrolyzed species caused by the electrolysis.

A "counter electrode" refers to an electrode paired with the working electrode, through which passes an electrochemical current equal in magnitude and opposite in sign to the current passed through the working electrode. In the context of the invention, the term "counter electrode" is meant to include counter electrodes which also function as reference electrodes (i.e. a counter/reference electrode).

An "electrochemical sensor" is a device configured to detect the presence and/or measure the concentration of an analyte via electrochemical oxidation and reduction reactions on the sensor. These reactions are transduced to an electrical signal that can be correlated to an amount or concentration of analyte.

"Electrolysis" is the electrooxidation or electroreduction of a compound either directly at an electrode or via one or more electron transfer agents.

The term "facing electrodes" refers to a configuration of the working and counter electrodes in which the working surface of the working electrode is disposed in approximate opposition to a surface of the counter electrode and where the distance between the working and counter electrodes is less than the width of the working surface of the working electrode.

A compound is "immobilized" on a surface when it is entrapped on or chemically bound to the surface.

The "measurement zone" is defined herein as a region of the sample chamber sized to contain only that portion of the sample that is to be interrogated during the analyte assay.

A "non-leachable" or "non-releasable" compound is a compound which does not substantially diffuse away from the working surface of the working electrode for the duration of the analyte assay.

A "redox mediator" is an electron transfer agent for carrying electrons between the analyte and the working electrode, either directly, or via a second electron transfer agent.

A "second electron transfer agent" is a molecule which carries electrons between the redox mediator and the analyte.

"Sorbent material" is material which wicks, retains, or is wetted by a fluid sample in its void volume and which does not substantially prevent diffusion of the analyte to the electrode.

A "working electrode" is an electrode at which analyte is electrooxidized or electroreduced with or without the agency of a redox mediator.

A "working surface" is that portion of the working electrode which is coated with redox mediator and configured for exposure to sample.

The small volume, in vitro analyte sensors of the present invention are designed to measure the concentration of an analyte in a portion of a sample having a volume less than about 1 µL, preferably less than about 0.5 µL, more preferably less than about 0.2 µL, and most preferably less than about 0.1 µL. The analyte of interest is typically provided in a solution or biological fluid, such as blood or serum. Referring to the Drawings in general and FIGS. 1-4 in particular, a small volume, in vitro electrochemical sensor 20 of the invention generally includes a working electrode 22, a counter (or counter/reference) electrode 24, and a sample chamber 26 (see FIG. 4). The sample chamber 26 is configured so that when a sample is provided in the chamber the sample is in electrolytic contact with both the working electrode 22 and the counter electrode 24. This allows electrical current to flow between the electrodes to effect the electrolysis (electrooxidation or electroreduction) of the analyte.

Working Electrode

The working electrode 22 may be formed from a molded carbon fiber composite or it may consist of an inert non-conducting base material, such as polyester, upon which a suitable conducting layer is deposited. The conducting layer should have relatively low electrical resistance and should be electrochemically inert over the potential range of the sensor during operation. Suitable conductors include gold, carbon, platinum, ruthenium dioxide and palladium, as well as other non-corroding materials known to those skilled in the art. The electrode and/or conducting layers are deposited on the surface of the inert material by methods such as vapor deposition or printing.

A tab 23 may be provided on the end of the working electrode 22 for easy connection of the electrode to external electronics (not shown) such as a voltage source or current measuring equipment. Other known methods or structures may be used to connect the working electrode 22 to the external electronics.

Sensing Layer and Redox Mediator

A sensing layer 32 containing a non-leachable (i.e., non-releasable) redox mediator is disposed on a portion of the working electrode 22. Preferably, there is little or no leaching of the redox mediator away from the working electrode 22 into the sample during the measurement period, which is typically less than about 5 minutes. More preferably, the redox mediators of the present invention are bound or otherwise immobilized on the working electrode 22 to prevent undesirable leaching of the mediator into the sample. A diffusing or leachable (i.e., releasable) redox mediator is not desirable when the working and counter electrodes are close together (i.e., when the electrodes are separated by less than about 1 mm), because a large background signal is typically produced as the unbound mediator shuttles electrons between the working and counter electrodes, rather than between the analyte and the working electrode. This and other problems have hindered the development of low resistance cells and increased the minimum sample size required for determination of analyte concentration.

Application of sensing layer 32 on working electrode 22 creates a working surface on that electrode. In general, the working surface is that portion of the working electrode 22 coated with mediator and able to contact a fluid sample. If a portion of the sensing layer 32 is covered by a dielectric or other material, then the working surface will only be that portion of the electrode covered by redox mediator and exposed for contact with the sample.

The redox mediator mediates a current between the working electrode 22 and the analyte and enables the electrochemical analysis of molecules which are not suited for direct electrochemical reaction on an electrode. The mediator functions as an electron transfer agent between the electrode and the analyte.

Almost any organic or organometallic redox species can be used as a redox mediator. In general, the preferred redox mediators are rapidly reducible and oxidizable molecules having redox potentials a few hundred millivolts above or below that of the standard calomel electrode (SCE), and typically not more reducing than about −100 mV and not more oxidizing than about +400 mV versus SCE. Examples of organic redox species are quinones and quinhydrones and species that in their oxidized state have quinoid structures, such as Nile blue and indophenol. Unfortunately, some quinones and partially oxidized quinhydrones react with functional groups of proteins such as the thiol groups of cysteine, the amine groups of lysine and arginine, and the phenolic groups of tyrosine which may render those redox species unsuitable for some of the sensors of the present invention, e.g., sensors that will be used to measure analyte in biological fluids such as blood.

In general, mediators suitable for use in the invention have structures which prevent or substantially reduce the diffusional loss of redox species during the period of time that the sample is being analyzed. The preferred redox mediators include a redox species bound to a polymer which can in turn be immobilized on the working electrode. Useful redox mediators and methods for producing them are described in U.S. Pat. Nos. 5,264,104; 5,356,786; 5,262,035; and 5,320,725, herein incorporated by reference. Although, any organic or organometallic redox species can be bound to a polymer and used as a redox mediator, the preferred redox species is a transition metal compound or complex. The preferred transition metal compounds or complexes include osmium, ruthenium, iron, and cobalt compounds or complexes. The most preferred are osmium compounds and complexes.

One type of non-releasable polymeric redox mediator contains a redox species covalently bound in a polymeric composition. An example of this type of mediator is poly(vinylferrocene).

Alternatively, a suitable non-releasable redox mediator contains an ionically-bound redox species. Typically, these mediators include a charged polymer coupled to an oppositely charged redox species. Examples of this type of mediator include a negatively charged polymer such as Nafion® (Dupont) coupled to a positively charged redox species such as an osmium or ruthenium polypyridyl cation. Another example of an ionically-bound mediator is a positively charged polymer such as quaternized poly(4-vinyl pyridine) or poly(1-vinyl imidazole) coupled to a negatively charged redox species such as ferricyanide or ferrocyanide.

In another embodiment of the invention, the suitable non-releasable redox mediators include a redox species coordinatively bound to the polymer. For example, the mediator may be formed by coordination of an osmium or cobalt 2, 2'-bipyridyl complex to poly(1-vinyl imidazole) or poly(4-vinyl pyridine).

The preferred redox mediators are osmium transition metal complexes with one or more ligands having a nitrogen-containing heterocycle such as 2,2'-bipyridine, 1, 10-phenanthroline or derivatives thereof. Furthermore, the preferred redox mediators also have one or more polymeric ligands having at least one nitrogen-containing heterocycle, such as pyridine, imidazole, or derivatives thereof. These preferred mediators exchange electrons rapidly between each other and the electrodes so that the complex can be rapidly oxidized and reduced.

In particular, it has been determined that osmium cations complexed with two ligands containing 2,2'-bipyridine, 1,10-phenanthroline, or derivatives thereof, the two ligands not necessarily being the same, and further complexed with a polymer having pyridine or imidazole functional groups form particularly useful redox mediators in the small volume sensors of the present invention. Preferred derivatives of 2,2'-bipyridine for complexation with the osmium cation are 4,4'-dimethyl-2,2'-bipyridine and mono-, di-, and polyalkoxy-2,2'-bipyridines, such as 4,4'-dimethoxy-2,2'-bipyridine, where the carbon to oxygen ratio of the alkoxy groups is sufficient to retain solubility of the transition metal complex in water. Preferred derivatives of 1,10-phenanthroline for complexation with the osmium cation are 4,7-dimethyl-1,10-phenanthroline and mono-, di-, and polyalkoxy-1,10-phenanthrolines, such as 4,7-dimethoxy-1,10-phenanthroline, where the carbon to oxygen ratio of the alkoxy groups is sufficient to retain solubility of the transition metal complex in water Preferred polymers for complexation with the osmium cation include poly(1-vinyl imidazole) e.g., PVI, and poly(4-vinyl pyridine), e.g., PVP, either alone or with a copolymer. Most preferred are redox mediators with osmium complexed with poly(1-vinyl imidazole) alone or with a copolymer.

The preferred redox mediators have a redox potential between about −150 mV to about +400 mV versus the standard calomel electrode (SCE). Preferably, the potential of the redox mediator is between about −100 mV and +100 mV and more preferably, the potential is between about −50 mV and +50 mV. The most preferred redox mediators have osmium redox centers and a redox potential more negative than +100 mV versus SCE, more preferably the redox potential is more negative than +50 mV versus SCE, and most preferably is near −50 mV versus SCE.

It is also preferred that the redox mediators of the inventive sensors be air-oxidizable. This means that the redox mediator is oxidized by air, preferably so that at least 90% of the mediator is in an oxidized state prior to introduction of sample into the sensor. Air-oxidizable redox mediators include osmium cations complexed with two mono-, di-, or polyalkoxy-2,2'-bipyridine or mono-, di-, or polyalkoxy-1,10-phenanthroline ligands, the two ligands not necessarily being the same, and further complexed with polymers having pyridine and imidazole functional groups. In particular, $Os[4,4'\text{-dimethoxy-2,2'-bipyridine}]_2Cl^{+/+2}$ complexed with poly(4-vinyl pyridine) or poly(1-vinyl imidazole) attains approximately 90% or more oxidation in air.

In a preferred embodiment of the invention, the sensing layer 32 includes a second electron transfer agent which is capable of transferring electrons to or from the redox mediator and the analyte. One example of a suitable second electron transfer agent is an enzyme which catalyzes a reaction of the analyte. For example, a glucose, oxidase or glucose dehydrogenase, such as pyrroloquinoline quinone glucose dehydrogenase (PQQ), is used when the analyte is glucose. A lactate oxidase fills this role when the analyte is lactate. These enzymes catalyze the electrolysis of an analyte by transferring electrons between the analyte and the electrode via the redox mediator. Preferably, the second electron transfer agent is non-leachable, and more preferably immobilized on the electrode, to prevent unwanted leaching of the agent into the sample. This is accomplished, for example, by cross linking the second electron transfer agent with the redox mediator, thereby providing a sensing layer with non-leachable components.

Figure 4:
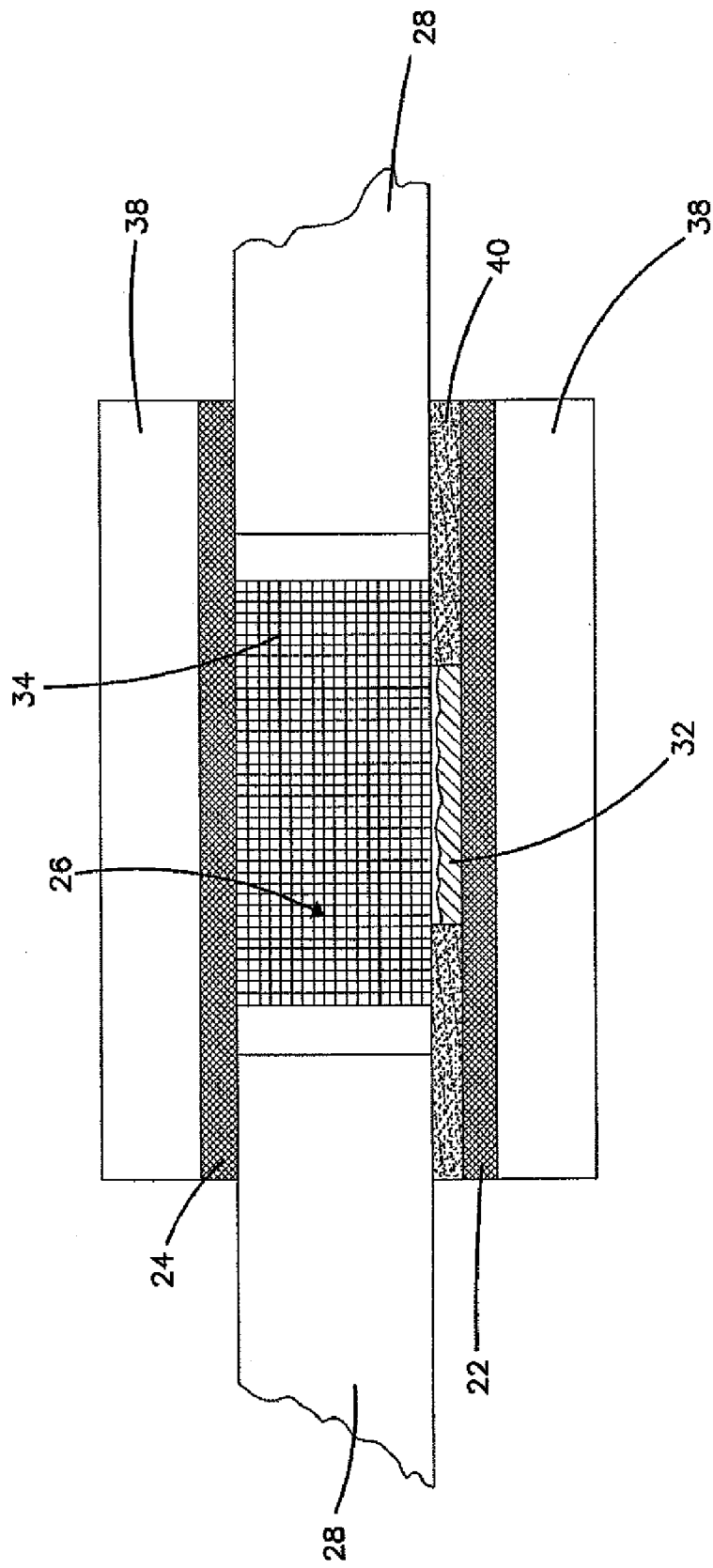
FIG. 4 is a not-to-scale side-sectional drawing of a portion of the sensor of FIG. 1 or 3 showing the relative positions of the redox mediator, the sample chamber, and the electrodes.

To prevent electrochemical reactions from occurring on portions of the working electrode not coated by the mediator, a dielectric 40 may be deposited on the electrode over, under, or surrounding the region with the bound redox mediator, as shown in FIG. 4. Suitable dielectric materials include waxes and non-conducting organic polymers such as polyethylene. Dielectric 40 may also cover a portion of the redox mediator on the electrode. The covered portion of the mediator will not contact the sample, and, therefore, will not be a part of the electrode's working surface.

Counter Electrode

Counter electrode 24 may be constructed in a manner similar to working electrode 22. Counter electrode 24 may also be a counter/reference electrode. Alternatively, a separate reference electrode may be provided in contact with the sample chamber. Suitable materials for the counter/reference or reference electrode include Ag/AgCl printed on a non-conducting base material or silver chloride on a silver metal base. If the counter electrode is not a reference electrode, the same materials and methods may be used to make the counter electrode as are available for constructing the working electrode 22, however, no redox mediator is immobilized on the counter or counter/reference electrode 24. A tab 25 may be provided on the electrode for convenient connection to the external electronics (not shown), such as a coulometer or other measuring device.

Figure 3:
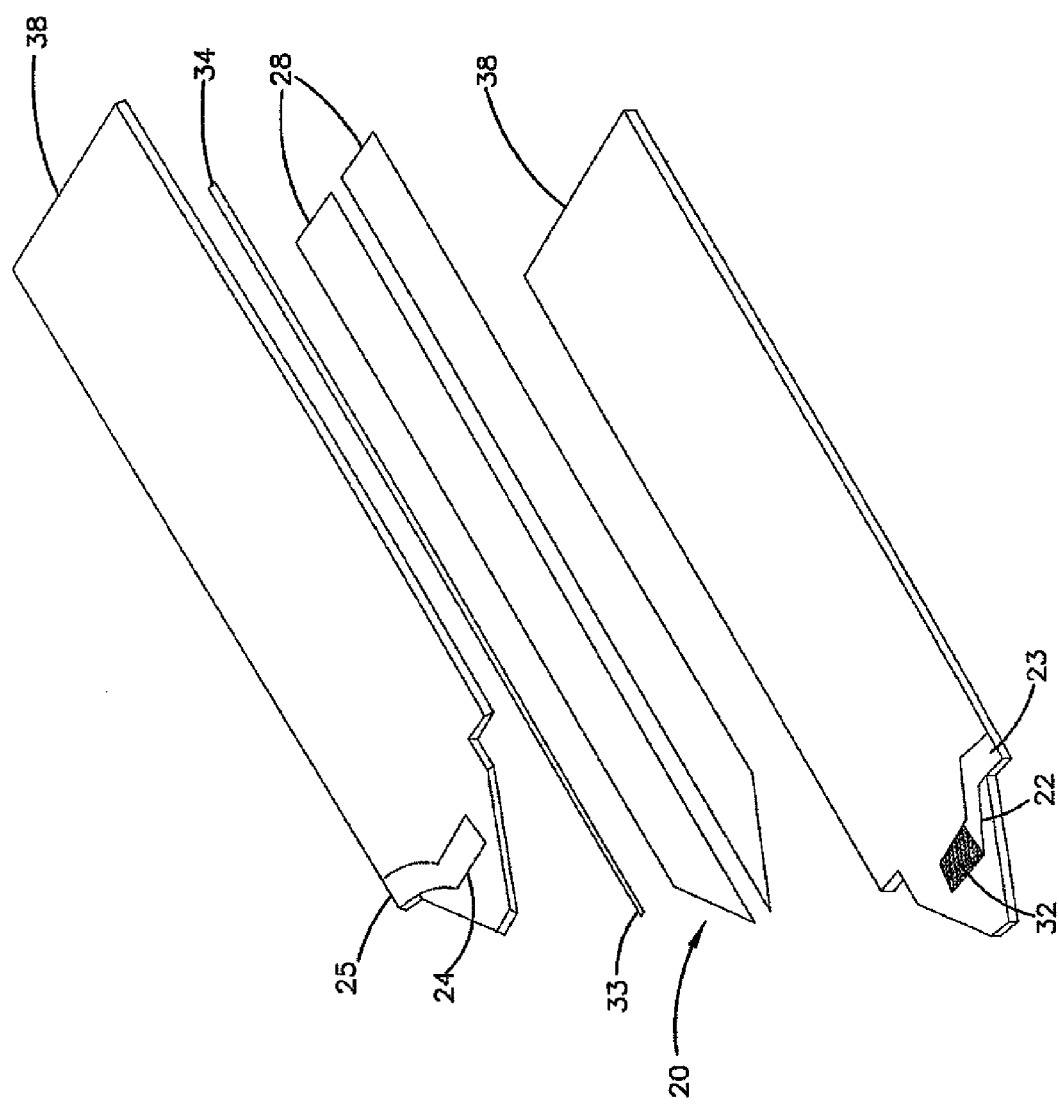
FIG. 3 is a schematic view of a third embodiment of an electrochemical sensor in accordance with the principles of the present invention having a working electrode and a counter electrode facing each other and having an extended sample chamber.

In one embodiment of the invention, working electrode 22 and counter electrode 24 are disposed opposite to and facing each other to form a facing electrode pair as depicted in FIGS. 1 and 3. In this preferred configuration, the sample chamber 26 is typically disposed between the two electrodes. For this facing electrode configuration, it is preferred that the electrodes are separated by a distance of less than about 0.2 mm, preferably less than 0.1 mm, and most preferably less than 0.05 mm.

The electrodes need not be directly opposing each other, they may be slightly offset. Furthermore, the two electrodes need not be the same size. Preferably, the counter electrode 24 is at least as large as the working surface of the working electrode 22. The counter electrode 22 can also be formed with tines in a comb shape. Other configuration of both the counter electrode and working electrode are within the scope of the invention. However, the separation distance between any portion of the working electrode and some portion of the counter electrode preferably does not exceed the limits specified hereinabove.

Figure 2:
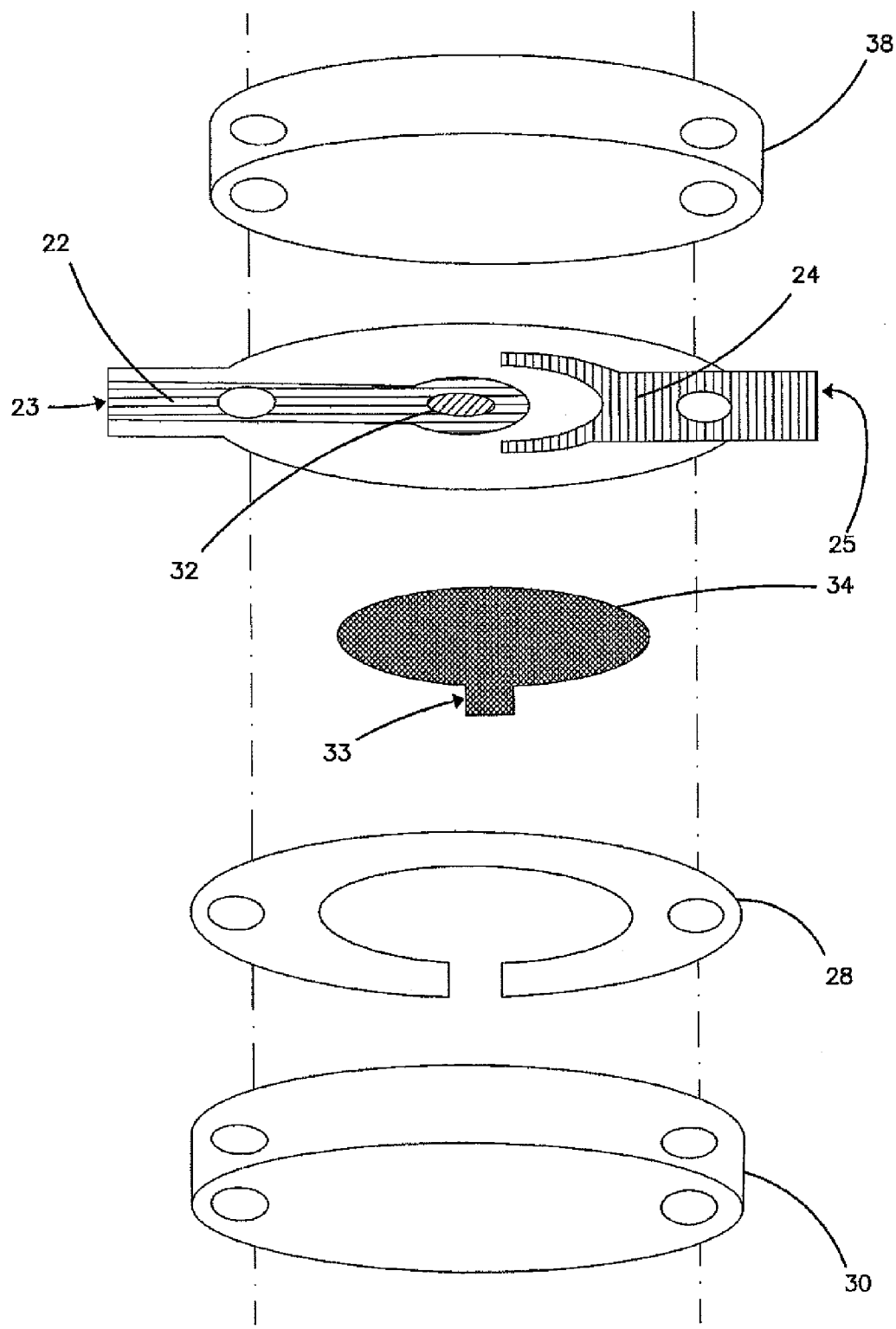
FIG. 2 is a schematic view of a second embodiment of an electrochemical sensor in accordance with the principles of the present invention having a working electrode and a counter electrode in a coplanar configuration.

In another embodiment of the invention, the two electrodes 22, 24 are coplanar as shown in FIG. 2. In this case, the sample chamber 26 is in contact with both electrodes and is bounded on the side opposite the electrodes by a non-conducting inert base 30. Suitable materials for the inert base include non-conducting materials such as polyester.

Other configurations of the inventive sensors are also possible. For example, the two electrodes may be formed on surfaces that make an angle to each other. One such configuration would have the electrodes on surfaces that form a right angle. Another possible configuration has the electrodes on a curved surface such as the interior of a tube. The working and counter electrodes may be arranged so that they face each other from opposite sides of the tube. This is another example of a facing electrode pair. Alternatively, the electrodes may be placed near each other on the tube wall (e.g., one on top of the other or side-by-side).

In any configuration, the two electrodes must be configured so that they do not make direct electrical contact with each other, to prevent shorting of the electrochemical sensor. This may be difficult to avoid when the facing electrodes having a short (less than 100 µm) distance between them.

A spacer 28 can be used to keep the electrodes apart when the electrodes face each other as depicted in FIGS. 1 and 3. The spacer is typically constructed from an inert non-conducting material such as polyester, Mylar™, Kevlar™ or any other strong, thin polymer film, or, alternatively, a thin polymer film such as a Teflon™ film, chosen for its chemical inertness. In addition to preventing contact between the electrodes, the spacer 28 often functions as a portion of the boundary for the sample chamber 26 as shown in FIGS. 1-4.

Sample Chamber

The sample chamber 26 is typically defined by a combination of the electrodes 22, 24, an inert base 30, and a spacer 28 as shown in FIGS. 1-4. A measurement zone is contained within this sample chamber and is the region of the sample chamber that contains only that portion of the sample that is interrogated during the analyte assay. In the embodiment of the invention illustrated in FIGS. 1 and 2, sample chamber 26 is the space between the two electrodes 22, 24 and/or the inert base 30. In this embodiment, the sample chamber has a volume that is preferably less than about 1 µL, more preferably less than about 0.5 µL, and most preferably less than about 0.2 µL. In the embodiment of the invention depicted in FIGS. 1 and 2, the measurement zone has a volume that is approximately equal to the volume of the sample chamber.

Figure 5:
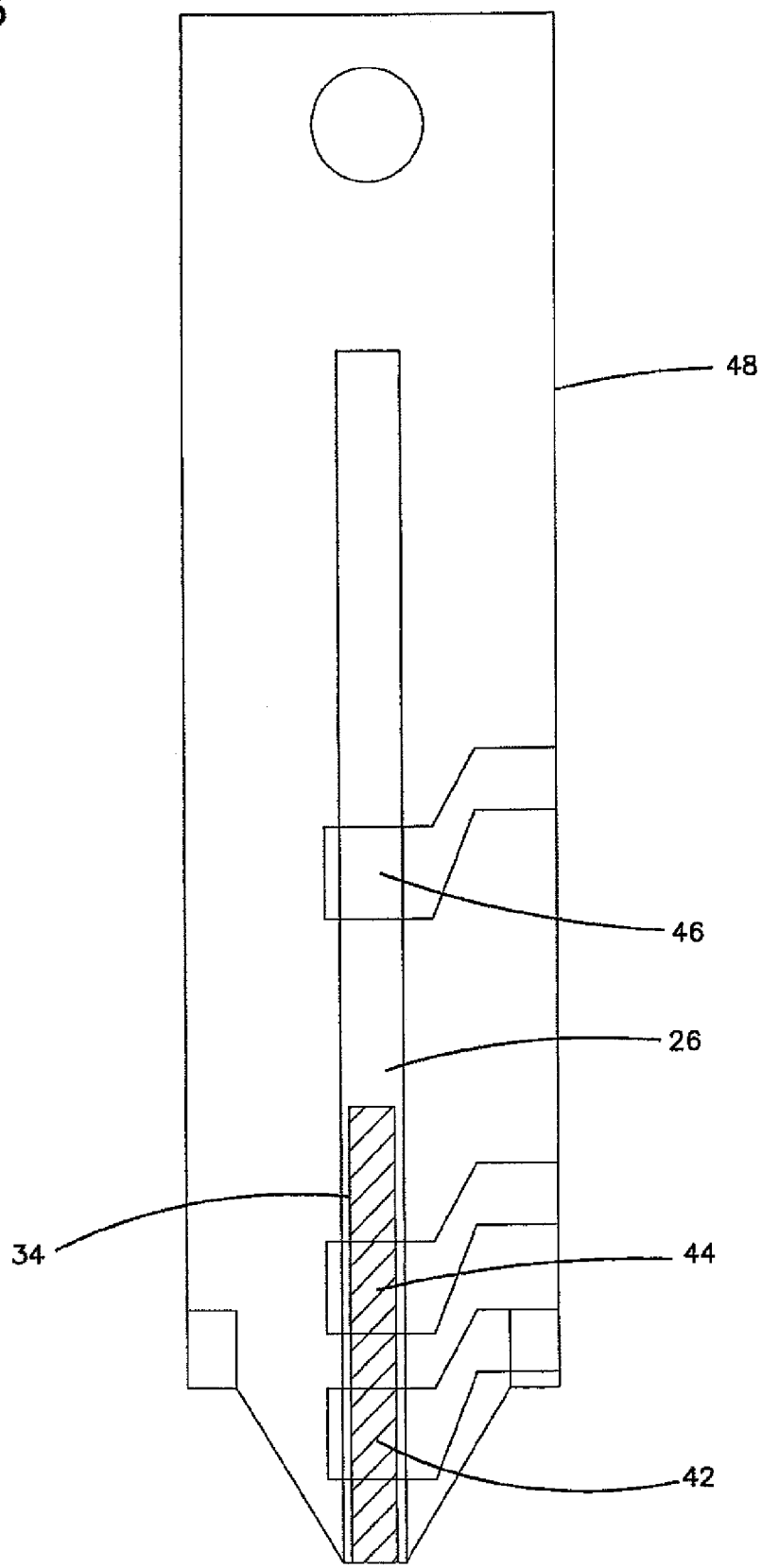
FIG. 5 is a top view of an embodiment of a multiple electrode sensor in accordance with the principles of the present invention.

In another embodiment of the invention, shown in FIG. 3, sample chamber 26 includes much more space than the region proximate electrodes 22, 24. This configuration makes it possible to provide multiple electrodes in contact with one or more sample chambers, as shown in FIG. 5. In this embodiment, sample chamber 26 is preferably sized to contain a volume of less than about 1 µL, more preferably less than about 0.5 µL, and most preferably less than about 0.2 µL. The measurement zone (i.e., the region containing the volume of sample to be interrogated) is generally sized to contain a volume of sample of less than about 1 µL, preferably less than about 0-5 µL, more preferably less than about 0.2 µL, and most preferably less than about 0.1 µL. One particularly useful configuration of this embodiment positions working electrode 22 and counter electrode 24 facing each other, as shown in FIG. 3. In this embodiment, the measurement zone, corresponding to the region containing the portion of the sample which will be interrogated, is the portion of sample chamber 26 bounded by the working surface of the working electrode and disposed between the two facing electrodes. When the surface of the working electrode is not entirely covered by redox mediator, the measurement zone is the space between the two facing electrodes that has a surface area corresponding to the working surface (i.e., redox mediator-covered surface) of working electrode 22 and a thickness corresponding to the separation distance between working electrode 22 and counter electrode 24.

In both of the embodiments discussed above, the thickness of the sample chamber and of the measurement zone correspond typically to the thickness of spacer 28 (e.g., the distance between the electrodes in FIGS. 1 and 3, or the distance between the electrodes and the inert base in FIG. 2). Preferably, this thickness is small to promote rapid electrolysis of the analyte, as more of the sample will be in contact with the electrode surface for a given sample volume. In addition, a thin sample chamber helps to reduce errors from diffusion of analyte into the measurement zone from other portions of the sample chamber during the analyte assay, because diffusion time is long relative to the measurement time. Typically, the thickness of the sample chamber is less than about 0.2 mm. Preferably, the thickness of the sample chamber is less than about 0.1 mm and, more preferably, the thickness of the sample chamber is about 0.05 mm or less.

The sample chamber may be empty before the sample is placed in the chamber. Alternatively, the sample chamber may include a sorbent material 34 to sorb and hold a fluid sample during the measurement process. Suitable sorbent materials include polyester, nylon, cellulose, and cellulose derivatives such as nitrocellulose. The sorbent material facilitates the uptake of small volume samples by a wicking action which may complement or, preferably, replace any capillary action of the sample chamber.

One of the most important functions of the sorbent material is to reduce the volume of fluid needed to fill the sample chamber and corresponding measurement zone of the sensor. The actual volume of sample within the measurement zone is partially determined by the amount of void space within the sorbent material. Typically, suitable sorbents consist of about 5% to about 50% void space. Preferably, the sorbent material consists of about 10% to about 25% void space.

The displacement of fluid by the sorbent material is advantageous. By addition of a sorbent, less sample is needed to fill sample chamber 26. This reduces the volume of sample that is required to obtain a measurement and also reduces the time required to electrolyze the sample.

The sorbent material 34 may include a tab 33 which is made of the same material as the sorbent and which extends from the sensor, or from an opening in the sensor, so that a sample may be brought into contact with tab 33, sorbed by the tab, and conveyed into the sample chamber 26 by the wicking action of the sorbent material 34. This provides a preferred method for directing the sample into the sample chamber 26. For example, the sensor may be brought into contact with a region of an animal (including human) that has been pierced with a lancet to draw blood. The blood is brought in contact with tab 33 and drawn into sample chamber 26 by the wicking action of the sorbent 34. The direct transfer of the sample to the sensor is especially important when the sample is very small, such as when the lancet is used to pierce a portion of the animal that is not heavily supplied with near-surface capillary vessels and furnishes a blood sample volume of less than 1 μL.

Methods other than the wicking action of a sorbent may be used to transport the sample into the sample chamber or measurement zone. Examples of such means for transport include the application of pressure on a sample to push it into the sample chamber, the creation of a vacuum by a pump or other vacuum-producing means in the sample chamber to pull the sample into the chamber, capillary action due to interfacial tension of the sample with the walls of a thin sample chamber, as well as the wicking action of a sorbent material.

The sensor can also be used in conjunction with a flowing sample stream. In this configuration, the sample stream is made to flow through a sample chamber. The flow is stopped periodically and the concentration of the analyte is determined by electrochemical method, such as coulometry. After the measurement, the flow is resumed, thereby removing the sample from the sensor. Alternatively, sample may flow through the chamber at a very slow rate, such that all of the analyte is electrolyzed in transit, yielding a current dependent only upon analyte concentration and flow rate.

The entire sensor assembly is held firmly together to ensure that the sample remains in contact with the electrodes and that the sample chamber and measurement zone maintain the same volume. This is an important consideration in the coulometric analysis of a sample, where measurement of a defined sample volume is needed. One method of holding the sensor together is depicted in FIGS. 1 and 2. Two plates 38 are provided at opposite ends of the sensor. These plates are typically constructed of non-conducting materials such as plastics. The plates are designed so that they can be held together with the sensor between the two plates. Suitable holding devices include adhesives, clamps, nuts and bolts, screws, and the like.

Integrated Sample Acquisition and Analyte Measurement Device

Figure 6:
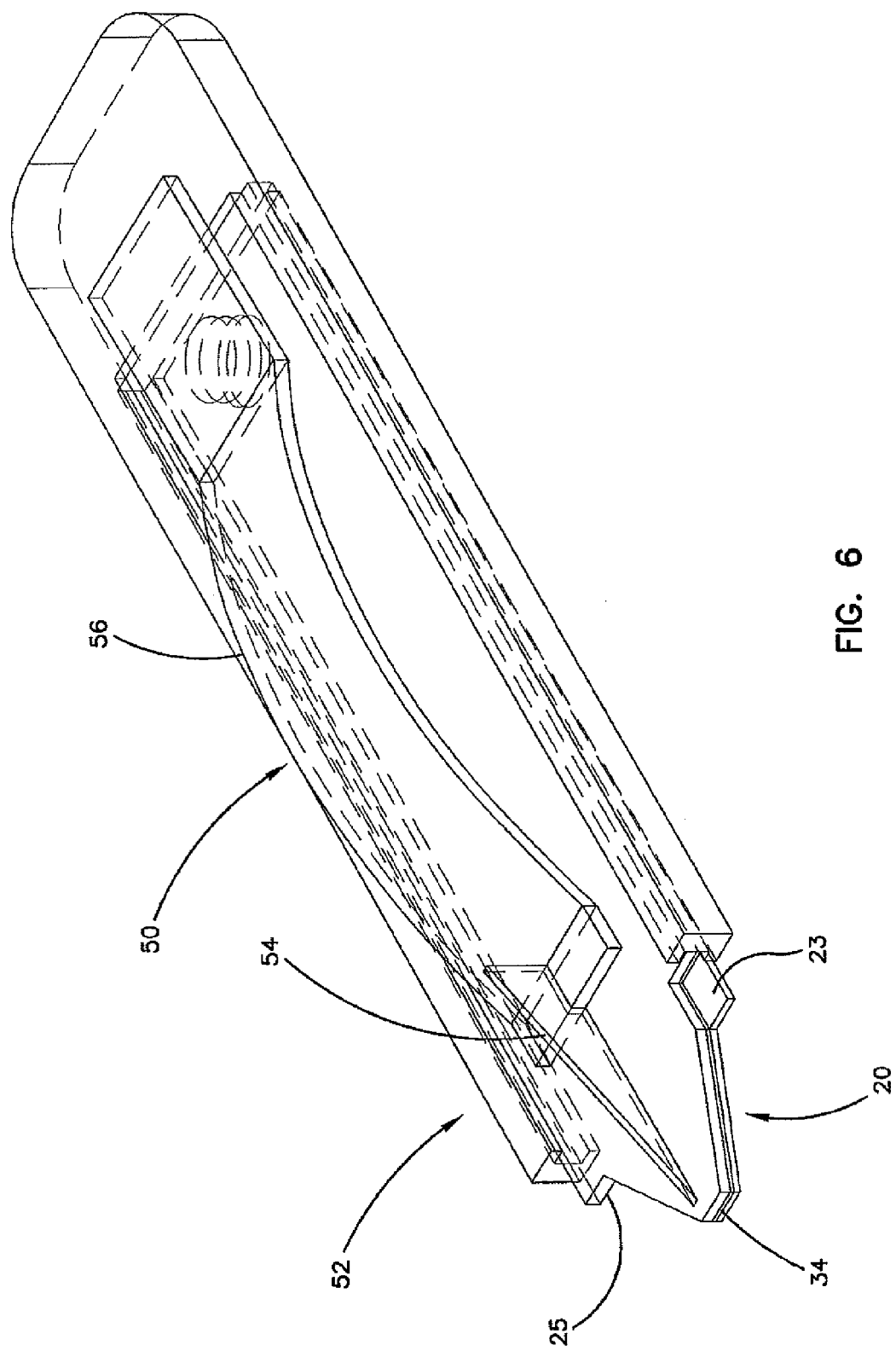
FIG. 6 is a perspective view of an embodiment of an analyte measurement device in accordance with the principles of the present invention having a sample acquisition means and the sensor of FIG. 4.

In a preferred embodiment of the invention, an analyte measurement device 52 constructed according to the principles of the present invention includes a sensor 20, as described hereinabove, combined with a sample acquisition means 50 to provide an integrated sampling and measurement device. The sample acquisition means 50 illustrated in FIG. 6, includes, for example, a skin piercing member 54, such as a lancet, attached to a resilient deflectable strip 56 (or other similar device, such as a spring) which may be pushed to inject the lancet into a patient's skin to cause blood flow.

The resilient strip 56 is then released and the skin piercing member 54 retracts. Blood flowing from the area of skin pierced by member 54 can then be transported, for example, by the wicking action of sorbent material 34, into sensor 20 for analysis of the analyte. The analyte measurement device 52 may then be placed in a reader, not shown, which connects a coulometer or other electrochemical analysis equipment to the electrode tabs 23, 25 to determine the concentration of the analyte by electroanalytical means.

Operation of the Sensor

An electrochemical sensor of the invention is operated in the following manner. A potential is applied across the working and counter electrodes. The magnitude of the required potential is dependent on the redox mediator. The potential at an electrode where the analyte is electrolyzed is typically large enough to drive the electrochemical reaction to or near completion, but the magnitude of the potential is, preferably, not large enough to induce significant electrochemical reaction of interferents, such as urate, ascorbate, and acetaminophen, that may affect the current measurements. Typically the potential is between about −150 mV and about +400 mV versus the standard calomel electrode (SCE). Preferably, the potential of the redox mediator is between about −100 mV and +100 mV and, more preferably, the potential is between about −50 mV and +50 mV.

The potential may be applied either before or after the sample has been placed in the sample chamber. The potential is preferably applied after the sample has come to rest in the sample chamber to prevent electrolysis of sample passing through the measurement zone as the sample chamber is filling. When the potential is applied and the sample is in the measurement zone, an electrical current will flow between the working electrode and the counter electrode. The current is a result of the electrolysis of the analyte in the sample. This electrochemical reaction occurs via the redox mediator and the optional second electron transfer agent. For many biomolecules, B the process is described by the following reaction equations:

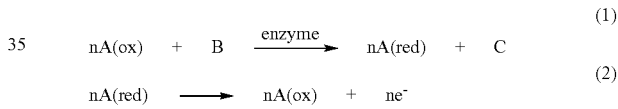

Biochemical B is oxidized to C by redox mediator species A in the presence of an appropriate enzyme. Then the redox mediator A is oxidized at the electrode. Electrons are collected by the electrode and the resulting current is measured.

As an example, one sensor of the present invention is based on the reaction of a glucose molecule with two non-leachable ferricyanide anions in the presence of glucose oxidase to produce two non-leachable ferrocyanide anions, two protons and gluconolactone. The amount of glucose present is assayed by electrooxidizing the non-leachable ferrocyanide anions to non-leachable ferricyanide anions and measuring the total charge passed.

Those skilled in the art will recognize that there are many different reaction mechanisms that will achieve the same result; namely the electrolysis of an analyte through a reaction pathway incorporating a redox mediator. Equations (1) and (2) are a non-limiting example of such a reaction.

In a preferred embodiment of the invention, coulometry is used to determine the concentration of the analyte. This measurement technique utilizes current measurements obtained at intervals over the course of the assay, to determine analyte concentration. These current measurements are integrated over time to obtain the amount of charge, Q, passed to or from the electrode. Q is then used to calculate the concentration of the analyte by the following equation:

$$[\text{analyte}] = Q/nFV \qquad (3)$$

where n is the number of electron equivalents required to electrolyze the analyte, F is Faraday's constant (approximately 96,500 coulombs per equivalent), and V is the volume of sample in the measurement zone.

In one embodiment of the invention, the analyte is completely or nearly completely electrolyzed. The charge is then calculated from current measurements made during the electrochemical reaction and the concentration of the analyte is determined using equation (3). The completion of the electrochemical reaction is typically signaled when the current reaches a steady-state value. This indicates that all or nearly all of the analyte has been electrolyzed. For this type of measurement, at least 90% of the analyte is typically electrolyzed, preferably, at least 95% of the analyte is electrolyzed and, more preferably, at least 99% of the analyte is electrolyzed.

For this method it is desirable that the analyte be electrolyzed quickly. The speed of the electrochemical reaction depends on several factors, including the potential that is applied between the electrodes and the kinetics of reactions (1) and (2). (Other significant factors include the size of the measurement zone and the presence of sorbent in the measurement zone.) In general, the larger the potential, the larger the current through the cell (up to a transport limited maximum) and therefore, the faster the reaction will typically occur. However, if the potential is too large, other electrochemical reactions may introduce significant error in the measurement. Typically, the potential between the electrodes as well as the specific redox mediator and optional second electron transfer agent are chosen so that the analyte will be almost completely electrolyzed in less than 5 minutes, based on the expected concentration of the analyte in the sample. Preferably, the analyte will be almost completely electrolyzed within about 2 minutes and, more preferably, within about 1 minute.

In another embodiment of the invention, the analyte is only partially electrolyzed. The current is measured during the partial reaction and then extrapolated using mathematical techniques known to those skilled in the art to determine the current curve for the complete or nearly complete electrolysis of the analyte. Integration of this curve yields the amount of charge that would be passed if the analyte were completely or nearly completely electrolyzed and, using equation (3), the concentration of the analyte is calculated.

The above described methods are based on coulometric analyses, due to the advantages of coulometric measurements, as described hereinbelow. However, those skilled in the art will recognize that a sensor of the invention may also utilize potentiometric, amperometric, voltammetric, and other electrochemical techniques to determine the concentration of an analyte in a sample. There are, however, disadvantages to using some of these techniques. The measurements obtained by these non-coulometric methods are not temperature independent as the current and potential obtained by the electrolysis of an analyte on an electrode is very sensitive to sample temperature. This presents a problem for the calibration of a sensor which will be used to measure bioanalytes and other samples at unknown or variable temperatures.

In addition, the measurements obtained by these non-coulometric electrochemical techniques are sensitive to the amount of enzyme provided in the sensor. If the enzyme deactivates or decays over time, the resulting measurements will be affected. This will limit the shelf life of such sensors unless the enzyme is very stable.

Finally, the measurements obtained by non-coulometric electrochemical techniques such as amperometry will be negatively affected if a substantial portion of the analyte is electrolyzed during the measurement period. An accurate steady-state measurement can not be obtained unless there is sufficient analyte so that only a relatively small portion of the analyte is electrolyzed during the measurement process.

The electrochemical technique of coulometry overcomes these problems. Coulometry is a method for determining the amount of charge passed or projected to pass during complete or nearly complete electrolysis of the analyte. One coulometric technique involves electrolyzing the analyte on a working electrode and measuring the resulting current between the working electrode and a counter electrode at two or more times during the electrolysis. The electrolysis is complete when the current reaches a steady state. The charge used to electrolyze the sample is then calculated by integrating the measured currents over time. Because the charge is directly related to the amount of analyte in the sample there is no temperature dependence of the measurement. In addition, the activity of the redox mediator does not affect the value of the measurement, but only the time required to obtain the measurement (i.e., less active redox mediator requires a longer time to achieve complete electrolysis of the sample) so that decay of the mediator over time will not render the analyte concentration determination inaccurate. And finally, the depletion of the analyte in the sample by electrolysis is not a source of error, but rather the objective of the technique. (However, the analyte need not be completely electrolyzed if the electrolysis curve is extrapolated from the partial electrolysis curve based on well-known electrochemical principles.)

For coulometry to be an effective measurement technique for determining the concentration of an analyte in a sample, it is necessary to accurately determine the volume of the measured sample. Unfortunately, the volume of the sample in the measurement zone of a small volume sensor (i.e., less than one micro liter) may be difficult to accurately determine because the manufacturing tolerances of one or more dimensions of the measurement zone may have significant variances.

Air-Oxidizable Redox Mediators

Another source of error in a coulometric sensor is the presence of electrochemical reactions other than those associated with the analyte. In a sensor having a redox mediator, a potential source of measurement error is the presence of redox mediator in an unknown mixed oxidation state (i.e., mediator not reproducibly in a known oxidation state). Redox mediator will then be electrolyzed at the electrode, not in response to the presence of an analyte, but simply due to its initial oxidation state. Referring to equations (1) and (2), current not attributable to the oxidation of biochemical B will flow due to oxidation of a portion of a redox mediator, A, that is in its reduced form prior to the addition of the sample. Thus, it is important to know the oxidation state of the analyte prior to introduction of the sample into the sensor. Furthermore, it is desirable that all or nearly all of the redox mediator be in a single oxidation state prior to the introduction of the sample into the sensor.

Each redox mediator has a reduced form or state and an oxidized form or state. In one aspect of the invention, it is preferred that the amount of redox mediator in the reduced form prior to the introduction of sample be significantly smaller than the expected amount of analyte in a sample in order to avoid a significant background contribution to the measured current. In this embodiment of the invention, the molar amount of redox mediator in the reduced form prior to the introduction of the analyte is preferably less tan, on a stoichiometric basis, about 10%, and more preferably less than about 5%, and most preferably less than 1%, of the molar amount of analyte for expected analyte concentrations. (The molar amounts of analyte and redox mediator should be compared based on the stoichiometry of the applicable redox reaction so that if two moles of redox mediator are needed to electrolyze one mole of analyte, then the molar amount of redox mediator in the reduced form prior to introduction of the analyte is preferably less than 20% and more preferably less than about 10% and most preferably less than about 2% of the molar amount of analyte for expected analyte concentrations.) Methods for controlling the amount of reduced mediator are discussed below.

In another aspect of the invention, it is preferred that the relative ratio of oxidized redox mediator to reduced redox mediator prior to introduction of the sample in the sensor be relatively constant between similarly constructed sensors. The degree of variation in this ratio between similarly constructed sensors will negatively affect the use of a calibration curve to account for the reduced mediator, as significant variations between sensors will make the calibration less reliable. For this aspect of the invention, the percentage of the redox mediator in the reduced form prior to introduction of the sample in the sensor varies by less than about 20% and preferably less than about 10% between similarly constructed sensors.

One method of controlling the amount of reduced redox mediator prior to the introduction of the sample in the sensor is to provide an oxidizer to oxidize the reduced form of the mediator. One of the most convenient oxidizers is $O_2$. Oxygen is usually readily available to perform this oxidizing function. Oxygen can be supplied by exposing the sensor to air. In addition, most polymers and fluids absorb $O_2$ from the air unless special precautions are taken. Typically, at least 90% of an air-oxidizable (i.e., $O_2$ oxidizable) mediator is in the oxidized state upon storage or exposure to air for a useful period of time, e.g., one month or less, and preferably, one week or less, and, more preferably, one day or less.

Suitable mediators which are both air-oxidizable (i.e., $O_2$-oxidizable) and have electron transfer capabilities have been described hereinabove. One particular family of useful mediators are osmium complexes which are coordinated or bound to ligands with one or more nitrogen-containing heterocycles. In particular, osmium complexed with mono-, di-, and polyalkoxy-2,2'-bipyridine or mono-, di-, and polyalkoxy-1,10-phenanthroline, where the alkoxy groups have a carbon to oxygen ratio sufficient to retain solubility in water, are air-oxidizable. These osmium complexes typically have two substituted bipyridine or substituted phenanthroline ligands, the two ligands not necessarily being identical. These osmium complexes are further complexed with a polymeric ligand with one or more nitrogen-containing heterocycles, such as pyridine and imidazole. Preferred polymeric ligands include poly(4-vinyl pyridine) and, more preferably, poly(1-vinyl imidazole) or copolymers thereof. Os[4,4'-dimethoxy-2,2'-bipyridine]$_2$Cl$^{+/+2}$ complexed with a poly(1-vinyl imidazole) or poly(4-vinyl pyridine) has been shown to be particularly useful as the Os$^{+2}$ cation is oxidizable by $O_2$ to Os$^{+3}$. Similar results are expected for complexes of Os[4,7-dimethoxy-1,10-phenanthroline]$_2$Cl$^{+/+2}$, and other mono-, di-, and polyalkoxy bipyridines and phenanthrolines, with the same polymers.

A complication associated with air-oxidizable mediators arises if the air oxidation of the redox mediator is so fast that a substantial portion of the analyte-reduced redox mediator is oxidized by $O_2$ during an analyte assay. This will result in an inaccurate assay as the amount of analyte will be underestimated because the mediator will be oxidized by the oxidizer rather than by electrooxidation at the electrode. Thus, it is preferred that the reaction of the redox mediator with $O_2$ proceeds more slowly than the electrooxidation of the mediator. Typically, less than 5%, and preferably less than 1%, of the reduced mediator should be oxidized by the oxidizer during an assay.

The reaction rate of the air oxidation of the mediator can be controlled through choice of an appropriate complexing polymer. For example, the oxidation reaction is much faster for Os [4,4'-dimethoxy-2,2'-bipyridine]$_2$Cl$^{+/+2}$ coordinatively coupled to poly(1-vinyl imidazole) than for the same Os complex coupled to poly(4-vinyl pyridine) The choice of an appropriate polymer will depend on the expected analyte concentration and the potential applied between the electrodes, both of which determine the rate of the electrochemical reaction.

Thus, in one embodiment of the invention, the preferred redox mediator has the following characteristics: 1) the mediator does not react with any molecules in the sample or in the sensor other than the analyte (optionally, via a second electron transfer agent); 2) nearly all of the redox mediator is oxidized by an oxidizer such as $O_2$ prior to introduction of the sample in the sensor; and 3) the oxidation of the redox mediator by the oxidizer is slow compared to the electrooxidation of the mediator by the electrode.

Alternatively, if the redox mediator is to be oxidized in the presence of the analyte and electroreduced at the electrode, a reducer rather than an oxidizer would be required. The same considerations for the appropriate choice of reducer and mediator apply as described hereinabove for the oxidizer.

The use of stable air-oxidizable redox mediators in the electrochemical sensors of the invention provides an additional advantage during storage and packaging. Sensors of the invention which include air oxidizable redox mediators can be packaged in an atmosphere containing molecular oxygen and stored for long periods of time, e.g., greater than one month, while maintaining more than 80% and preferably more than 90% of the redox species in the oxidized state.

Optical Sensors

The air-oxidizable redox species of the present invention can be used in other types of sensors. The osmium complexes described hereinabove are suitable for use in optical sensors, due to the difference in the absorption spectra and fluorescence characteristics of the complexed Os$^{+2}$ and Os$^{+3}$ species. Absorption, transmission, reflection, or fluorescence measurements of the redox species will correlate with the amount of analyte in the sample (after reaction between an analyte and the redox species, either directly, or via a second electron transfer agent such as an enzyme). In this configuration, the molar amount of redox mediator should be greater, on a stoichiometric basis, than the molar amount of analyte reasonably expected to fill the measurement zone of the sensor.

Standard optical sensors, including light-guiding optical fiber sensors, and measurement techniques can be adapted for use with the air-oxidizable mediators For example, the optical sensors of the invention may include a light-transmitting or light reflecting support on which the air-oxidizable redox species, and preferably an analyte-responsive enzyme, is coated to form a film. The support film forms one boundary for the measurement zone in which the sample is placed. The other boundaries of the measurement zone are determined by the configuration of the cell. Upon filling the measurement zone with an analyte-containing sample, reduction of the air-oxidizable mediator by the analyte, preferably via reaction with the analyte-responsive enzyme, causes a shift in the mediator's oxidation state that is detected by a change in the light transmission, absorption, or reflection spectra or in the fluorescence of the mediator at one or more wavelengths of light.

Multiple Electrode Sensors and Calibration

Errors in assays may occur when mass produced sensor are used because of variations in the volume of the measurement zone of the sensors. Two of the three dimensions of the measurement zone, the length and the width, are usually relatively large, between about 1-5 mm. Electrodes of such dimensions can be readily produced with a variance of 2% or less. The submicroliter measurement zone volume requires, however, that the third dimension be smaller than the length or width by one or two order of magnitude. As mentioned hereinabove, the thickness of the sample chamber is typically between about 0.1 and about 0.01 mm. Manufacturing variances in the thickness may be as large or larger than the desired thickness. Therefore, it is desirable that a method be provided to accommodate for this uncertainty in the volume of sample within the measurement zone.

In one embodiment of the invention, depicted in FIG. 5, multiple working electrodes 42, 44, 46 are provided on a base material 48. These electrodes are covered by another base, not shown, which has counter electrodes, not shown, disposed upon it to provide multiple facing electrode pairs. The variance in the separation distance between the working electrode and the counter electrode among the electrode pairs on a given sensor is significantly reduced, because the working electrodes and counter electrodes are each provided on a single base with the same spacer 28 between each electrode pair (see FIG. 3).

One example of a multiple electrode sensor that can be used to accurately determine the volume of the measurement zones of the electrode pairs and also usefull in reducing noise is presented herein. In this example, one of the working electrodes 42 is prepared with a non-leachable redox mediator and a non-leachable second electron transfer agent (e.g., an enzyme). Sorbent material may be disposed between that working electrode 42 and its corresponding counter electrode. Another working electrode 44 includes non-leachable redox mediator, but no second electron transfer agent on the electrode. Again, this second electrode pair may have sorbent material between the working electrode 44 and the corresponding counter electrode. An optional third working electrode 46 has no redox mediator and no second electron transfer agent bound to the electrode, nor is there sorbent material between the working electrode 46 and its corresponding counter electrode.

The thickness of the sample chamber can be determined by measuring the capacitance, preferably in the absence of any fluid, between electrode 46 (or any of the other electrodes 42, 44 in the absence of sorbent material) and its corresponding counter electrode. The capacitance of an electrode pair depends on the surface area of the electrodes, the interelectrode spacing, and the dielectric constant of the material between the plates. The dielectric constant of air is unity which typically means that the capacitance of this electrode configuration is a few picofarads (or about 100 picofarads if there is fluid between the electrode and counter electrode given that the dielectric constant for most biological fluids is approximately 75). Thus, since the surface area of the electrodes are known, measurement of the capacitance of the electrode pair allows for the determination of the thickness of the measurement zone to within about 1-5%.

The amount of void volume in the sorbent material, can be determined by measuring the capacitance between electrode 44 (which has no second electron transfer agent) and its associated counter electrode, both before and after fluid is added. Upon adding fluid, the capacitance increases markedly since the fluid has a much larger dielectric constant. Measuring the capacitance both with and without fluid allows the determination of the spacing between the electrodes and the void volume in the sorbent, and thus the volume of the fluid in the reaction zone.

The sensor error caused by redox mediator in a non-uniform oxidation state prior to the introduction of the sample can be measured by concurrently electrolyzing the sample in the measurement zones that are proximate electrodes 42 and 44. At electrode 42, the analyte is electrolyzed to provide the sample signal. At electrode 44, the analyte is not electrolyzed because of the absence of the second electron transfer agent (assuming that a second electron transfer agent is necessary). However, a small charge will pass (and a small current will flow) due to the electrolysis of the redox mediator that was in a mixed oxidation state (i.e., some redox centers in the reduced state and some in the oxidized state) prior to the introduction of the sample. The small charge passed between the electrodes in this second electrode pair can be subtracted from the charge passed between the first electrode pair to substantially remove the error due to the oxidation state of the redox mediator. This procedure also reduces the error associated with other electrolyzed interferents, such as ascorbate, urate, and acetaminophen.

Other electrode configurations can also use these techniques (i.e., capacitance measurements and coulometric measurements in the absence of a critical component) to reduce background noise and error due to interferents and imprecise knowledge of the volume of the interrogated sample. Protocols involving one or more electrode pairs and one or more of the measurements described above can be developed and are within the scope of the invention. For example, only one electrode pair is needed for the capacitance measurements, however, additional electrode pairs may be used for convenience.

EXAMPLES

The invention will be further characterized by the following examples. These examples are not meant to limit the scope of the invention which has been fully set forth in the foregoing description. Variations within the concepts of the invention are apparent to those skilled in the art.

Example 1

Preparation of a Small Volume In Vitro Sensor for the Determination of Glucose Concentration A sensor was constructed corresponding to the embodiment of the invention depicted in FIG. 1. The working electrode was constructed on a Mylar™ film (DuPont), the Mylar™ film having a thickness of 0.175 mm and a diameter of about 2.5 cm. An approximately 12 micron thick carbon pad having a diameter of about 1 cm was screen printed on the Mylar™ film. The carbon electrode was overlaid with a water-insoluble dielectric insulator (Insulayer) having a thickness of 12 μm, and a 4 mm diameter opening in the center.

The center of the carbon electrode, which was not covered by the dielectric, was coated with a redox mediator. The redox mediator was formed by complexing poly(1-vinyl imidazole) with $Os(4,4'\text{-dimethoxy-}2,2'\text{-bipyridine})_2Cl_2$ followed by cross-linking glucose oxidase with the osmium polymer using polyethylene glycol diglycidyl ether as described in Taylor, et al., *J. Electroanal. Chem.*, 396:511 (1995). The ratio of osmium to imidazole functionalities in the redox mediator was approximately 1:15. The mediator was deposited on the working electrode in a layer having a thickness of 0.6 μm and a diameter of 4 mm. The coverage of the mediator on the electrode was about 60 μg/cm$^2$ (dry weight). A spacer material was placed on the electrode surrounding the mediator-covered surface of the electrode. The spacer was made of poly(tetrafluoroethylene) (PTFE) and had a thickness of about 0.040 mm.

A sorbent material was placed in contact with the mediator-covered surface of the working electrode. The sorbent was made of nylon (Tetko Nitex nylon 3-10/2) and had a diameter of 5 mm, a thickness of 0.045 mm, and a void volume of about 20%. The volume of sample in the measurement zone was calculated from the dimensions and characteristics of the sorbent and the electrode. The measurement zone had a diameter of 4 mm (the diameter of the mediator covered surface of the electrode) and a thickness of 0.045 mm (thickness of the nylon sorbent) to give a volume of 0.57 μL. Of this space, about 80% was filled with nylon and the other 20% was void space within the nylon sorbent. This resulting volume of sample within the measurement zone was about 0.11 μL.

A counter/reference electrode was placed in contact with the spacer and the side of the sorbent opposite to the working electrode so that the two electrodes were facing each other. The counter/reference electrode was constructed on a Mylar™ film having a thickness of 0.175 mm and a diameter of about 2.5 cm onto which a 12 micron thick layer of silver/silver chloride having a diameter of about 1 cm was screen printed.

The electrodes, sorbent, and spacer were pressed together using plates on either side of the electrode assembly. The plates were formed of polycarbonate plastic and were securely clamped to keep the sensor together. The electrodes were stored in air for 48 hours prior to use.

Tabs extended from both the working electrode and the counter/reference electrode and provided for an electrical contact with the analyzing equipment. A potentiostat was used to apply a potential difference of +200 mV between the working and counter/reference electrodes, with the working electrode being the anode. There was no current flow between the electrodes in the absence of sample, which was expected, as no conductive path between the electrodes was present.

The sample was introduced via a small tab of nylon sorbent material formed as an extension from the nylon sorbent in the sample chamber. Liquid was wicked into the sorbent when contact was made between the sample and the sorbent tab. As the sample chamber filled and the sample made contact with the electrodes, current flowed between the electrodes. When glucose molecules in the sample came in contact with the glucose oxidase on the working electrode, the glucose molecules were electrooxidized to gluconolactone. The osmium redox centers in the redox mediator then reoxidized the glucose oxidase. The osmium centers were in turn reoxidized by reaction with the working electrode. This provided a current which was measured and simultaneously integrated by a coulometer. (EG&G Princeton Applied Research Model #173)

The electrochemical reaction continued until the current reached a steady state value which indicated that greater than 95% of the glucose had been electroreduced. The current curve obtained by measurement of the current at specific intervals was integrated to determine the amount of charge passed during the electrochemical reaction. These charges were then plotted versus the known glucose concentration to produce a calibration curve.

The sensor was tested using 0.5 μL aliquots of solutions containing known concentrations of glucose in a buffer of artificial cerebrospinal fluid or in a control serum (Baxter-Dade, Monitrot Level 1, Miami, Fla.) in the range of 3 to 20 mM glucose. The artificial cerebrospinal fluid was prepared as a mixture of the following salts: 126 mM NaCl, 27.5 mM NaHCO$_3$, 2.4 mM KCl, 0.5 mM KH$_2$PO$_4$, 1.1 mM CaCl$_2$·2H$_2$O, and 0.5 mM Na$_2$SO$_4$.

Figure 7:
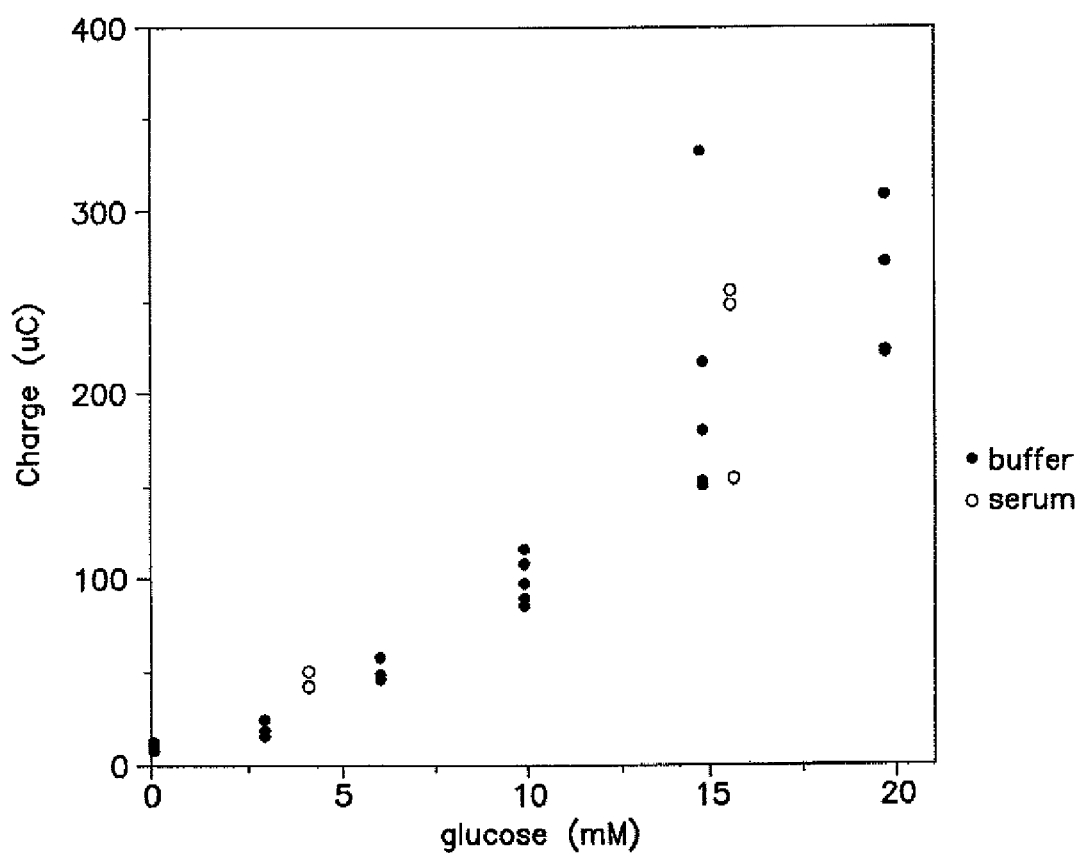
FIG. 7 is a graph of the charge required to electrooxidize a known quantity of glucose in an electrolyte buffered solution (filled circles) or serum solution (open circles) using the sensor of FIG. 1 with glucose oxidase as the second electron transfer agent.

The results of the analyses are shown in Table 1 and in FIG. 7. In Table 1, $Q_{avg}$ is the average charge used to electrolyze the glucose in 3-6 identical test samples (FIG. 7 graphs the charge for each of the test samples) and the 90% rise time corresponds to the amount of time required for 90% of the glucose to be electrolyzed. The data show a sensor precision of 10-20%, indicating adequate sensitivity of the sensor for low glucose concentrations, as well as in the physiologically relevant range (30 μg/dL-600 μg/dL).

TABLE 1

Sensor Results Using Glucose Oxidase

| | Number of Samples Tested | $Q_{avg}$ (μC) | 90% rise time (sec) |
|---|---|---|---|
| buffer only | 4 | 9.9 ± 1.8 | 13 ± 6 |
| 3 mM glucose/buffer | 5 | 17.8 ± 3.5 | 19 ± 5 |
| 6 mM glucose/buffer | 4 | 49.4 ± 4.9 | 25 ± 3 |
| 10 mM glucose/buffer | 6 | 96.1 ± 12.4 | 36 ± 17 |
| 15 mM glucose/buffer | 5 | 205.2 ± 75.7 | 56 ± 23 |
| 20 mM glucose/buffer | 4 | 255.7 ± 41.0 | 62 ± 17 |
| 4.2 mM glucose/serum | 3 | 44.2 ± 4.3 | 44 ± 3 |
| 15.8 mM glucose/serum | 3 | 218.2 ± 57.5 | 72 ± 21 |

Figure 8:
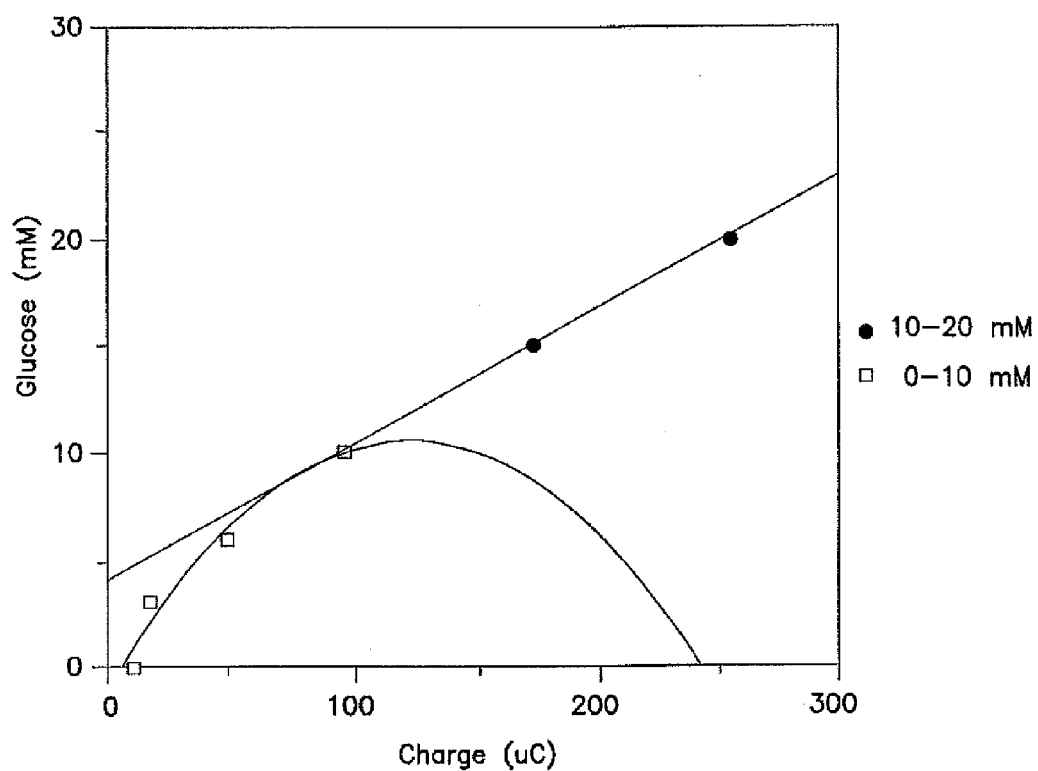
FIG. 8 is a graph of the average glucose concentrations for the data of FIG. 7 (buffered solutions only) with calibration curves calculated to fit the averages; a linear calibration curve was calculated for the 10-20 mM concentrations and a second order polynomial calibration curve was calculated for the 0-10 mM concentrations.

The average measured values of glucose concentration were fit by one or more equations to provide a calibration curve. FIG. 8 shows the calibration curves for the glucose/buffer data of Table 1. One of the 15.0 mM glucose measurements was omitted from these calculations because it was more than two standard deviations away from the average of the measurements. The higher glucose concentrations (10-20 mM) were fit by a linear equation. The lower glucose concentrations were fit by a second order polynomial.

Figure 9:
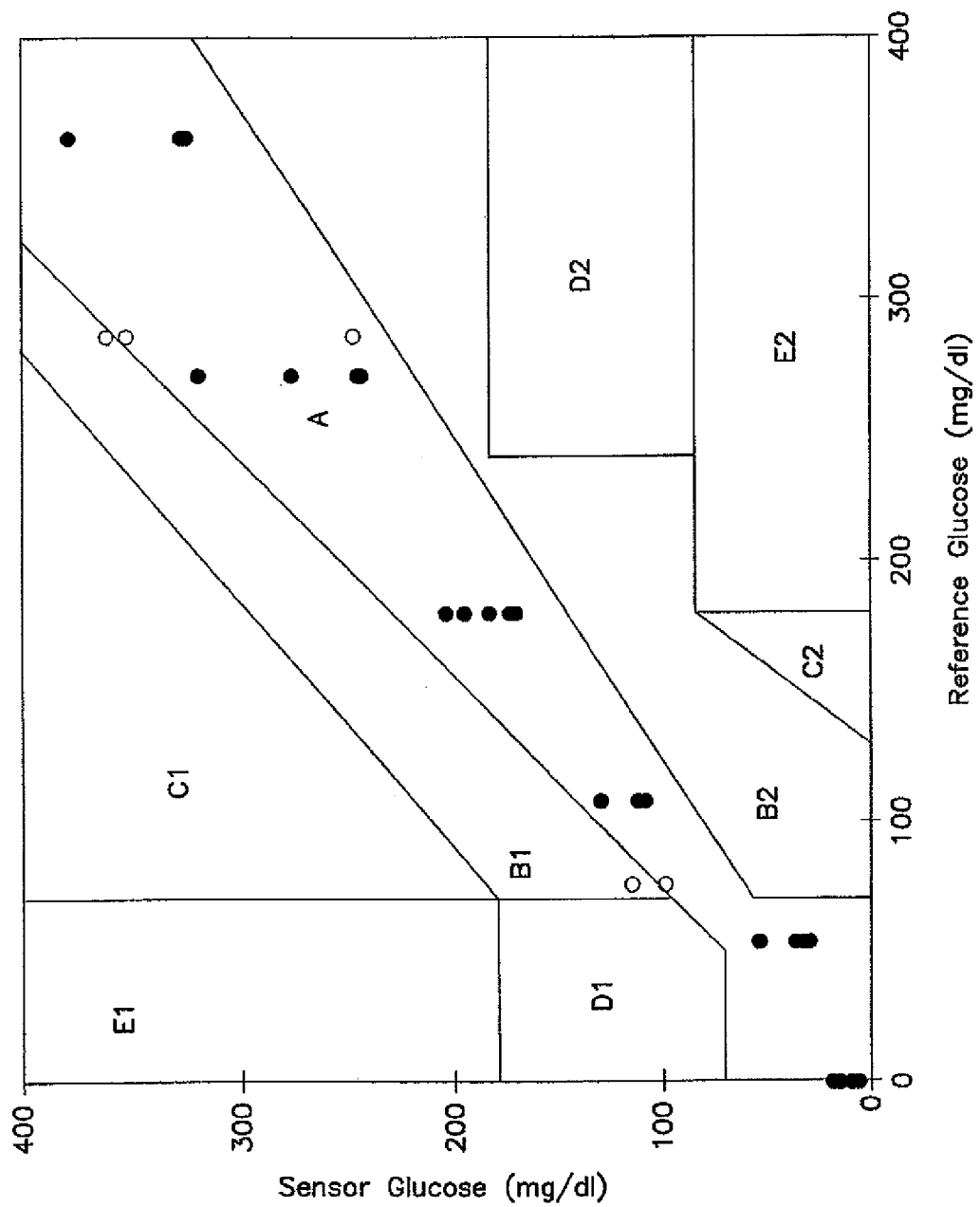
FIG. 9 is a Clarke-type clinical grid analyzing the clinical relevance of the glucose measurements of FIG. 7.

FIG. 9 shows the data of Table 1 plotted on an error grid developed by Clarke, et al. *Diabetes Care,* 5, 622-27, 1987, for the determination of the outcome of errors based on inaccurate glucose concentration determination. The graph plots "true" glucose concentration vs. measured glucose concentration, where the measured glucose concentration is determined by calculating a glucose concentration using the calibration curves of FIG. 8 for each data point of FIG. 7. Points in zone A are accurate, those in zone B are clinically acceptable, and those in zones C, D, and E lead to increasingly inappropriate and finally dangerous treatments.

There were 34 data points. Of those data points 91% fell in zone A, 6% in zone B, and 3% in zone C. Only one reading was determined to be in zone C. This reading was off-scale and is not shown in FIG. 9. Thus, 97% of the readings fell in the clinically acceptable zones A and B.

The total number of Os atoms was determined by reducing all of the Os and then electrooxidizing it with a glucose-free buffer in the sample chamber. This resulted in a charge of 59.6±5.4 μC. Comparison of this result with the glucose-free buffer result in Table 1 indicated that less than 20% of the Os is in the reduced form prior to introduction of the sample. The variability in the quantity of osmium in the reduced state is less than 5% of the total quantity of osmium present.

Example 2

Response of the Glucose Sensor to Interferents

A sensor constructed in the same manner as described above for Example 1 was used to determine the sensor's response to interferents. The primary electrochemical interferents for blood glucose measurements are ascorbate, acetaminophen, and urate. The normal physiological or therapeutic (in the case of acetaminophen) concentration ranges of these common interferents are:

ascorbate: 0.034-0.114 mM acetaminophen: 0.066-0.200 mM urate (adult male): 0.27-0.47 mM Tietz, in: *Textbook of Clinical Chemistry*, C. A. Burtis and E. R. Ashwood, eds., W.B. Saunders Co., Philadelphia 1994, pp. 2210-12.

Buffered glucose-free interferent solutions were tested with concentrations of the interferents at the high end of the physiological or therapeutic ranges listed above. The injected sample volume in each case was 0.5 µL. A potential of +100 mV or +200 mV was applied between the electrodes. The average charge ($Q_{avg}$) was calculated by subtracting an average background current obtained from a buffer-only (i.e., interferent-free) solution from an average signal recorded with interferents present. The resulting average charge was compared with the signals from Table 1 for 4 mM and 10 mM glucose concentrations to determine the percent error that would result from the interferent.

TABLE 2

Interferent Response of Glucose Sensors

| Solution | E (mV) | n | $Q_{avg}$ (µC) | Error @ 4 mM glucose | Error @ 10 mM glucose |
|---|---|---|---|---|---|
| 0.114 mM ascorbate | 100 | 4 | 0.4 | 2% | <1% |
| 0.114 mM ascorbate | 200 | 4 | −0.5 | 2% | <1% |
| 0.2 mM acetaminophen | 100 | 4 | 0.1 | <1% | <1% |
| 0.2 mM acetaminophen | 200 | 4 | 1.0 | 5% | 1% |
| 0.47 mM urate | 100 | 4 | 6.0 | 30% | 7% |
| 0.47 mM urate | 200 | 4 | 18.0 | 90% | 21% |

These results indicated that ascorbate and acetaminophen were not significant interferents for the glucose sensor configuration, especially for low potential measurements. However, urate provided significant interference. This interference can be minimized by calibrating the sensor response to a urate concentration of 0.37 mM, e.g., by subtracting an appropriate amount of charge as determined by extrapolation from these results from all glucose measurements of the sensor. The resulting error due to a 0.10 mM variation in urate concentration (the range of urate concentration is 0.27-0.47 in an adult male) would be about 6% at 4 mM glucose and 100 mV.

Example 3

Sensor with Glucose Dehydrogenase

A sensor similar to that described for Example 1 was prepared and used for this example, except that glucose oxidase was replaced by pyrroloquinoline quinone glucose dehydrogenase and a potential of only +100 mV was applied as opposed to the +200 mV potential in Example 1. The results are presented in Table 3 below and graphed in FIG. 10.

TABLE 3

Sensor Results Using Glucose Dehydrogenase

| | n | $Q_{avg}$ (µC) | 90% rise time (s) |
|---|---|---|---|
| buffer | 4 | 21.7 ± 5.2 | 14 ± 3 |
| 3 mM glucose/buffer | 4 | 96.9 ± 15.0 | 24 ± 6 |
| 6 mM glucose/buffer | 4 | 190.6 ± 18.4 | 26 ± 6 |
| 10 mM glucose/buffer | 4 | 327.8 ± 69.3 | 42 ± 9 |

The results indicated that the charge obtained from the glucose dehydrogenase sensor was much larger than for the comparable glucose oxidase sensor, especially for low concentrations of glucose. For 4 mM glucose concentrations the measurements obtained by the two sensors differed by a factor of five. In addition, the glucose dehydrogenase sensor operated at a lower potential, thereby reducing the effects of interferent reactions.

Figure 10:
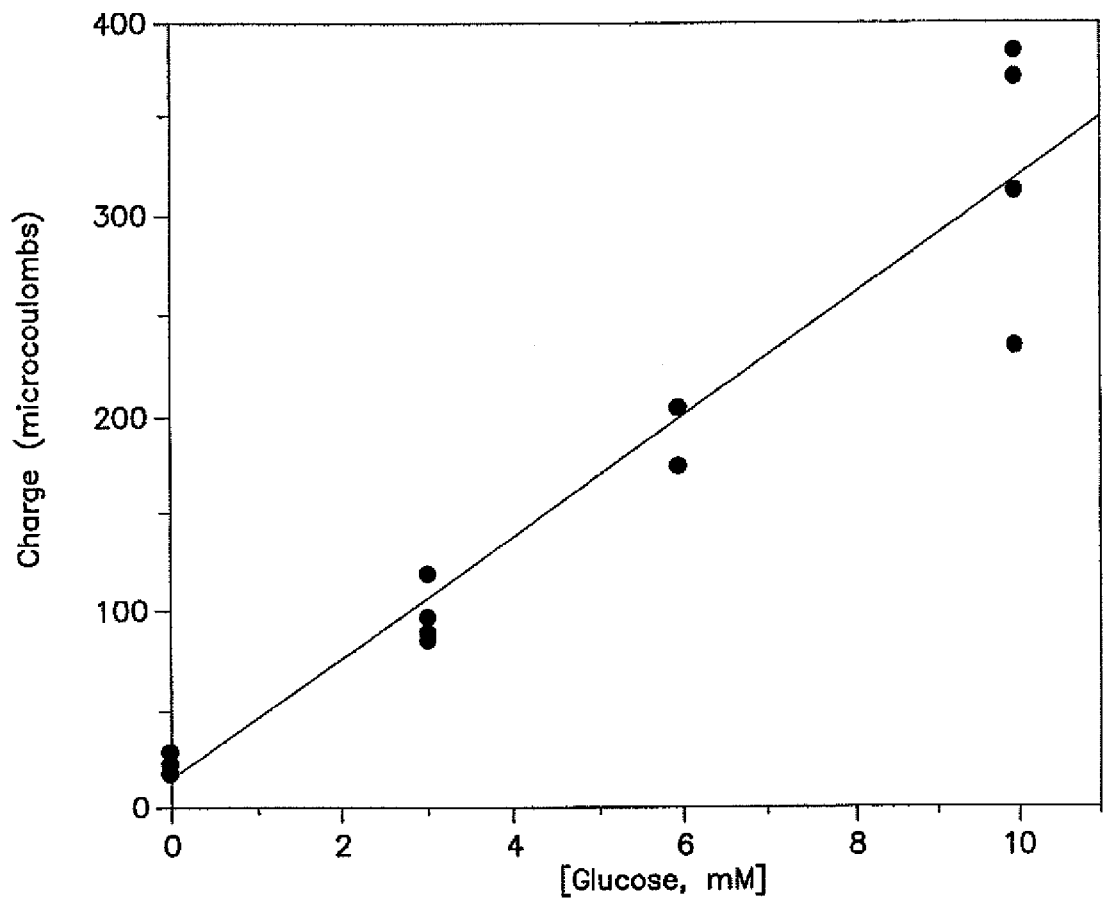
FIG. 10 is a graph of the charge required to electrooxidize a known quantity of glucose in an electrolyte buffered solution using the sensor of FIG. 1 with glucose dehydrogenase as the second electron transfer agent.

In addition, the results from Table 3 were all fit by a linear calibration curve as opposed to the results in Example 1, as shown in FIG. 10. A single linear calibration curve is greatly preferred to simplify sensor construction and operation.

Also, assuming that the interferent results from Table 2 are applicable for this sensor, all of the interferents would introduce an error of less than 7% for a 3 mM glucose solution at a potential of 100 mV.

Example 4

Determination of Lactate Concentration in a Fluid Stream

The sensor of this Example was constructed using a flow cell (BioAnalytical Systems, Inc. # MF-1025) with a glassy carbon electrode A redox mediator was coated on the electrode of the flow cell to provide a working electrode. In this case, the redox mediator was a polymer formed by complexing poly(1-vinyl imidazole) with Os(4,4'-dimethyl-2,2'-bipyridine)$_2$Cl$_2$ with a ratio of 1 osmium for every 15 imidazole functionalities. Lactate oxidase was cross-linked with the polymer via polyethylene glycol diglycidyl ether. The mediator was coated onto the electrode with a coverage of 500 µg/cm$^2$ and a thickness of 5 µm. The mediator was covered by a polycarbonate track-etched membrane (Osmonics-Poretics #10550) to improve adherence in the flow stream. The membrane was then overlaid by a single 50 µm thick spacer gasket (BioAnalytical Systems, Inc. #MF-1062) containing a void which defined the sample chamber and corresponding measurement zone. Assembly of the sensor was completed by attachment of a cell block (BioAnalytical Systems, Inc. #MF-1005) containing the reference and auxiliary electrodes of the flow cell.

The sample chamber in this case corresponded to a 50 µm thick cylinder (the thickness of the spacer gasket) in contact with a mediator-coated electrode having a surface area of 0.031 cm$^2$. The calculated volume of sample in the measurement zone of this sensor was approximately 0.16 µL.

The flow rate of the fluid stream was 5 µL/min. A standard three electrode potentiostat was attached to the cell leads and a potential of +200 mV was applied between the redox mediator-coated glassy carbon electrode and the reference electrode. This potential was sufficient to drive the enzyme-mediated oxidation of lactate.

As the fluid stream flowed through the sensor, a steady-state current proportional to the lactate concentration was measured. At periodic intervals the fluid flow was stopped and current was allowed to flow between the electrodes until approximately all of the lactate in the measurement zone was electrooxidized, as indicated by the achievement of a stabilized, steady-state current. The total charge. Q, required for lactate electrooxidation was found by integration of the differential current registered from the flow stoppage until the current reached a steady-state. The concentration was then calculated by the following equation:

$$[\text{lactate}] = Q/2FV \quad (4)$$

where V is the volume of sample within the measurement zone and F is Faraday's constant.

This assay was performed using lactate solutions having nominal lactate concentrations of 1.0, 5.0, and 10.0 mM. The measured concentrations for the assay were 1.9, 5.4, and 8.9 mM respectively.

Example 5

Determination of the Oxidation State of Os(4,4'-dimethoxy-2,2'-bipyridine)$_2$Cl$^{+/+2}$ Complexed with poly(1-vinyl imidazole)

A sensor having a three electrode design was commercially obtained from Ecossensors Ltd., Long Hanborough, England, under the model name "large area disposable electrode". The sensor contained parallel and coplanar working, reference and counter electrodes. The working surface area (0.2 cm 2) and counter electrodes were formed of printed carbon and the reference electrode was formed of printed Ag/AgCl. A redox mediator was coated on the carbon working electrode. The redox mediator was formed by complexation of poly(1-vinyl imidazole) with Os(4,4'-dimethoxy-2, 2'-bipyridine)$_2$Cl$_2$ in a ratio of 15 imidazole groups per Os cation followed by cross linking the osmium polymer with glucose oxidase using polyethylene glycol diglycidyl ether.

The electrode was cured at room temperature for 24 hours. The coplanar electrode array was then immersed in a buffered electrolyte solution, and a potential of +200 mV (sufficient for conversion of Os(II) to Os(III),) was applied between the working electrode and the reference electrode.

Upon application of the potential, an undetectable charge of less than 1 µC was passed. Subsequent reduction and reoxidation of the redox mediator yielded a charge for conversion of all Os from Os(II) to Os(III) of 65 µC. Therefore, more than 98% of the Os cations in the redox mediator were in the desired oxidized Os(III) state.

Example 6

Determination of the Oxidation State of the Os(4,4'-dimethoxy-2,2'-bipyridine)$_2$Cl$^{+/+2}$ Complexed with poly(4-vinyl pyridine)

A similar experiment to that of Example 5 was conducted with the same working/counter/reference electrode configuration except that the redox mediator on the working electrode was changed to a complex of Os(4,4'-dimethoxy-2,2'-bipyridine)$_2$Cl$_2$ with poly(4-vinyl pyridine), with 12 pyridine groups per Os cation, cross linked with glucose oxidase via polyethylene glycol diglycidyl ether.

Two sensors were constructed. The electrodes of the two sensors were cured at room temperature for 24 hours. The electrodes were then immersed in a buffered electrolyte solution and a potential of +200 mV was applied between the working and reference electrodes.

Upon application of the potential to the electrodes, a charge of 2.5 µC and 3.8 µC was passed in the two sensors, respectively. Subsequent reduction and reoxidation of the redox mediators yielded oxidation charges of 27.9 µC and 28.0 µC, respectively. Therefore, the sensors originally contained 91% and 86% of the Os cations in the desirable oxidized Os(III) state.

Example 7

Optical Sensor

An optical sensor is constructed by applying a film of redox polymer with crosslinked enzyme onto a light-transparent support such as a glass slide. The quantity of redox mediator is equal to or greater than (in a stoichiometric sense) the maximum quantity of analyte expected to fill the measurement zone. The spacer material, sorbent and facing support are securely clamped. The sample chamber is adapted to transmit light through the assembled sensor to an optical density detector or to a fluorescence detector. As sample fills the sample chamber and the redox mediator is oxidized, changes in the absorption, transmission, reflection or fluorescence of the redox mediator in the chamber are correlated to the amount of glucose in the sample.

Example 8

Blood Volumes from Upper Arm Lancet Sticks

The forearm of a single individual was pierced with a lancet multiple times in order to determine the reproducibility of blood volumes obtained by this method. Despite more than thirty lancet sticks in the anterior portion of each forearm and the dorsal region of the left forearm, the individual identified each stick as virtually painless.

The forearm was pierced with a Payless Color Lancet. The blood from each stick was collected using a 1 µL capillary tube, and the volume was determined by measuring the length of the blood column. The volumes obtained from each stick are shown below in Table 4.

TABLE 4

| | Volume of Lancet Sticks | | |
|---|---|---|---|
| | Left Anterior Forearm, (nL) | Right Anterior Forearm, (nL) | Left Dorsal Forearm, (nL) |
| 1 | 180 | 190 | 180 |
| 2 | 250 | 180 | 300 |
| 3 | 170 | 120 | 310 |
| 4 | 150 | 100 | 300 |
| 5 | 100 | 210 | 60 |
| 6 | 50 | 140 | 380 |
| 7 | 90 | 120 | 220 |
| 8 | 130 | 140 | 200 |
| 9 | 120 | 100 | 380 |
| 10 | | 100 | 320 |
| 11 | | | 260 |
| 12 | | | 250 |
| 13 | | | 280 |
| 14 | | | 260 |
| Avg. | 138 ± 58 nL | 140 ± 40 nL | 264 ± 83 nL |

The invention has been described with reference to various specific and preferred embodiments and techniques. However, it will be apparent to one of ordinarily skill in the art that many variations and modifications may be made while remaining within the spirit and scope of the invention.

All publications and patent applications in this specification are indicative of the level of ordinary skill in the art to which this invention pertains. All publications and patent applications are herein incorporated by reference to the same extent as if each individual publication or patent application was specifically and individually indicated by reference.

We claim:

1. A method for determining a concentration of an analyte in a body fluid of a patient, comprising the steps of:
   piercing a portion of the skin of a patient to create a flow of a body fluid;
   transporting 500 nl or less of the body fluid into an analyte sensor comprising two pairs of electrodes and a redox mediator, each pair of electrodes comprising a working electrode and a reference or counter electrode, wherein the sensor is configured and arranged for determining the concentration of the analyte from 500 nL or less of body fluid;
   holding the sample within the analyte sensor in a non-flow through manner such that the sample is in electrolytic contact with the pairs of electrodes; and
   determining by coulomtery the concentration of the analyte in the body fluid from the 500 nl or less of body fluid transported into the analyte sensor.

2. The method of claim 1, wherein the analyte sensor is configured and arranged for determining the concentration of the analyte from 200 nL or less of body fluid.

3. The method of claim 1, wherein the analyte sensor comprises a sample chamber that is configured and arranged to hold 200 nL or less of body fluid.

4. The method of claim 1, wherein the analyte sensor comprises a sample chamber that is configured and arranged to hold 100 nL or less of body fluid.

5. The method of claim 1, wherein the analyte sensor is configured and arranged for determining a concentration of the analyte from 100 nL or less of the body fluid.

6. The method of claim 1, wherein piercing a portion of the skin of a patient to create a flow of a body fluid comprises creating a flow of no more than 500 nL of a body fluid from the patient.

7. The method of claim 1, wherein piercing a portion of the skin of a patient to create a flow of a body fluid comprises creating a flow of no more than 200 nL of a body fluid from the patient.

8. The method of claim 1, wherein each pair of electrodes is a facing electrode pair.

9. The method of claim 1, wherein the sensor further includes a non-leachable enzyme on the working electrodes.

10. The method of claim 9, wherein the enzyme is immobilized on the working electrodes.

11. The method of claim 1, wherein the redox mediator is non-leachably disposed on the working electrodes.

12. The method of claim 11, wherein the redox mediator is immobilized on the working electrodes.

13. The method of claim 1, wherein the body fluid comprises blood.

14. The method of claim 1, wherein the body fluid consists essentially of blood.

15. The method of claim 1, wherein the analyte is glucose.

16. The method of claim 1, wherein transporting a portion of the body fluid into an analyte sensor comprises wicking a portion of the body fluid into the analyte sensor which comprises a sample chamber and a sorbent material disposed in the sample chamber for wicking the portion of the body fluid.

17. The method of claim 1, wherein transporting a portion of the body fluid into an analyte sensor comprises transporting, by capillary action, a portion of the body fluid into a sample chamber of the analyte sensor.

18. The method of claim 1, wherein transporting a portion of the body fluid into an analyte sensor comprises transporting, by application of a vacuum, a portion of the body fluid into a sample chamber of the analyte sensor.

19. The method of claim 1, wherein the analyte sensor comprises a sample chamber that is configured and arranged to hold 500 nL or less of body fluid.

20. The method of claim 1, wherein transporting a portion of the body fluid comprises transporting no more than 200 nL of the body fluid into the analyte sensor.

21. The method of claim 1, wherein the analyte sensor comprises three pairs of electrodes.

22. The method of claim 21, wherein each of said pairs of electrodes is a facing electrode pair.

23. The method of claim 21, wherein the sensor further includes a non-leachable enzyme on the working electrodes.

24. The method of claim 23, wherein the enzyme is immobilized on the working electrodes.

25. The method of claim 21, wherein the redox mediator is non-leachably disposed on the working electrodes.

26. The method of claim 25, wherein the redox mediator is immobilized on the working electrodes.

27. A method for determining a concentration of an analyte in a body fluid of a patient, comprising the steps of:
   piercing a portion of the skin of a patient to create a flow of a body fluid;
   transporting 500 nl or less of the body fluid into an analyte sensor comprising three pairs of electrodes and a redox mediator, each pair of electrodes comprising a working electrode and a reference or counter electrode, wherein the sensor is configured and arranged for determining the concentration of the analyte from 500 nL or less of body fluid;
   holding the sample within the analyte sensor in a non-flow through manner such that the sample is in electrolytic contact with the pairs of electrodes; and
   determining by coulometry the concentration of the analyte in the 500 nl or less of body fluid transported into the analyte sensor.

28. The method of claim 27, wherein the analyte sensor is configured and arranged for determining the concentration of the analyte from 200 nL or less of body fluid.

29. The method of claim 27, wherein the analyte sensor is configured and arranged for determining a concentration of the analyte from 100 nL or less of the body fluid.

30. The method of claim 27, wherein the analyte sensor comprises a sample chamber that is configured and arranged to hold 500 nL or less of body fluid.

31. The method of claim 27, wherein the analyte sensor comprises a sample chamber that is configured and arranged to hold 200 nL or less of body fluid.

32. The method of claim 27, wherein the analyte sensor comprises a sample chamber that is configured and arranged to hold 100 nL or less of body fluid.

33. The method of claim 27, wherein piercing a portion of the skin of a patient to create a flow of a body fluid comprises creating a flow of no more than 500 nL of a body fluid from the patient.

34. The method of claim 27, wherein piercing a portion of the skin of a patient to create a flow of a body fluid comprises creating a flow of no more than 200 nL of a body fluid from the patient.

35. The method of claim 27, wherein transporting a portion of the body fluid comprises transporting no more than 200 nL of the body fluid into the analyte sensor.

36. The method of claim 27, wherein transporting a portion of the body fluid into an analyte sensor comprises wicking a portion of the body fluid into the analyte sensor which comprises a sample chamber and a sorbent material disposed in the sample chamber for wicking the portion of the body fluid.

37. The method of claim 27, wherein transporting a portion of the body fluid into an analyte sensor comprises transporting, by capillary action, a portion of the body fluid into a sample chamber of the analyte sensor.

38. The method of claim 27, wherein transporting a portion of the body fluid into an analyte sensor comprises transporting, by application of a vacuum, a portion of the body fluid into a sample chamber of the analyte sensor.

39. The method of claim 27, wherein each pair of electrodes is a facing electrode pair.

40. A method for determining a concentration of an analyte in a body fluid of a patient, comprising the steps of:
piercing a portion of the skin of a patient to create a flow of a body fluid;
transporting 500 nl or less of the body fluid into an analyte sensor comprising one pair of electrodes and a redox mediator, the pair of electrodes comprising a working electrode and a reference or counter electrode, wherein the sensor is configured and arranged for determining the concentration of the analyte from 500 nL or less of body fluid;
holding the sample within the analyte sensor in a non-flow through manner such that the sample is in electrolytic contact with the pair of electrodes; and
determining by coulometry the concentration of the analyte in the 500 nl or less of body fluid transported into the analyte sensor.

41. The method of claim 40, wherein the analyte sensor is configured and arranged for determining the concentration of the analyte from 200 nL or less of body fluid.

42. The method of claim 40, wherein the analyte sensor is configured and arranged for determining a concentration of the analyte from 100 nL or less of the body fluid.

43. The method of claim 40, wherein the analyte sensor comprises a sample chamber that is configured and arranged to hold 500 nL or less of body fluid.

44. The method of claim 40, wherein the analyte sensor comprises a sample chamber that is configured and arranged to hold 200 nL or less of body fluid.

45. The method of claim 40, wherein the analyte sensor comprises a sample chamber that is configured and arranged to hold 100 nL or less of body fluid.

46. The method of claim 40, wherein piercing a portion of the skin of a patient to create a flow of a body fluid comprises creating a flow of no more than 500 nL of a body fluid from the patient.

47. The method of claim 40, wherein piercing a portion of the skin of a patient to create a flow of a body fluid comprises creating a flow of no more than 200 nL of a body fluid from the patient.

48. The method of claim 40, wherein transporting a portion of the body fluid comprises transporting no more than 200 nL of the body fluid into the analyte sensor.

49. The method of claim 40, wherein transporting a portion of the body fluid into an analyte sensor comprises wicking a portion of the body fluid into the analyte sensor which comprises a sample chamber and a sorbent material disposed in the sample chamber for wicking the portion of the body fluid.

50. The method of claim 40, wherein transporting a portion of the body fluid into an analyte sensor comprises transporting, by capillary action, a portion of the body fluid into a sample chamber of the analyte sensor.

51. The method of claim 40, wherein transporting a portion of the body fluid into an analyte sensor comprises transporting, by application of a vacuum, a portion of the body fluid into a sample chamber of the analyte sensor.

52. The method of claim 40, wherein the pair of electrodes is a facing electrode pair.

53. The method of claim 40, wherein the analyte sensor comprises glucose oxidase or glucose dehydrogenase.

54. The method of claim 40, wherein the redox mediator comprises an osmium complex, a ferrocyanide, or a ferricyanide.

55. The method of claim 40, wherein the working electrode is constructed of a material selected from gold, carbon, platinum, ruthenium dioxide and palladium.

56. The method of claim 40, wherein the working electrode is separated from the reference or counter electrode by a distance of less than 200 micrometer.

57. The method of claim 40, wherein the piercing comprise piercing the skin on a forearm of the patient.

* * * * *

UNITED STATES PATENT AND TRADEMARK OFFICE
CERTIFICATE OF CORRECTION

PATENT NO. : 8,142,642 B2
APPLICATION NO. : 12/182862
DATED : March 27, 2012
INVENTOR(S) : Adam Heller et al.

It is certified that error appears in the above-identified patent and that said Letters Patent is hereby corrected as shown below:

Claim 1, column 25, line 13, change "500 nl" to --500 nL--;

Claim 1, column 25, line 24, change "500 nl" to --500 nL--;

Claim 27, column 26, line 29, change "500 nl" to --500 nL--;

Claim 27, column 26, line 40, change "500 nl" to --500 nL--;

Claim 40, column 27, line 20, change "500 nl" to --500 nL--;

Claim 40, column 27, line 31, change "500 nl" to --500 nL--; and

Claim 56, column 28, line 40, change "micrometer" to --micrometers--.

Signed and Sealed this
Thirty-first Day of July, 2012

David J. Kappos
*Director of the United States Patent and Trademark Office*